US010485929B2

(12) United States Patent
Fuke et al.

(10) Patent No.: US 10,485,929 B2
(45) Date of Patent: Nov. 26, 2019

(54) LIQUID ADMINISTRATION DEVICE

(71) Applicant: Terumo Kabushiki Kaisha, Tokyo (JP)

(72) Inventors: Shigeaki Fuke, Fujinomiya (JP);
Masaomi Imai, Kofu (JP); Manabu Arinobe, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 518 days.

(21) Appl. No.: 14/846,524

(22) Filed: Sep. 4, 2015

(65) Prior Publication Data

US 2015/0374922 A1    Dec. 31, 2015

Related U.S. Application Data

(63) Continuation of application No. PCT/JP2014/054909, filed on Feb. 27, 2014.

(30) Foreign Application Priority Data

Mar. 8, 2013    (JP) .................................. 2013-047138

(51) Int. Cl.
*A61M 5/315*    (2006.01)
*A61M 5/32*    (2006.01)
(Continued)

(52) U.S. Cl.
CPC .... *A61M 5/31501* (2013.01); *A61M 5/31576* (2013.01); *A61M 5/31581* (2013.01);
(Continued)

(58) Field of Classification Search
CPC .... A61M 5/31501; A61M 2005/31508; A61M 5/31583; A61M 5/31586; A61M 5/315;
(Continued)

(56) References Cited

U.S. PATENT DOCUMENTS 5,084,017 A  *  1/1992  Maffetone ........... A61M 5/5066
                                                        604/110
2004/0054326 A1    3/2004  Hommann et al.
(Continued)

FOREIGN PATENT DOCUMENTS

JP       2013-506454 A       2/2013
WO    WO-2011/039216 A2     4/2011
(Continued)

OTHER PUBLICATIONS

International Search Report dated Jun. 10, 2014 issued in PCT/JP2014/054909.

*Primary Examiner* — Shefali D Patel
(74) *Attorney, Agent, or Firm* — Foley & Lardner LLP

(57) ABSTRACT

A liquid administration device includes: a structure that includes: a cylindrical body including a bottom part in a distal portion and an opening in a proximal portion, a needle tube positioned in the distal portion of the cylindrical body, the needle tube having a sharp needle tip at a distal end, wherein a proximal end of the needle tube is communicable with an inside of the cylindrical body, and a gasket installed in the cylindrical body, the gasket being slidable in an axial direction of the cylindrical body; an operation member configured to perform a pressing operation by pressing the gasket such that a liquid is discharged from the needle tube; a pressing mechanism configured to generate a pressing force for pressing the gasket; and a pressing force transmission inhibiting mechanism configured to inhibit transmission of the pressing force to the gasket during the pressing operation.

11 Claims, 13 Drawing Sheets

(51) Int. Cl.
*A61M 5/31* (2006.01)
*A61M 5/28* (2006.01)
*A61M 5/20* (2006.01)

(52) U.S. Cl.
CPC .... *A61M 5/31583* (2013.01); *A61M 5/31586* (2013.01); *A61M 5/288* (2013.01); *A61M 5/3157* (2013.01); *A61M 5/31513* (2013.01); *A61M 5/326* (2013.01); *A61M 5/3272* (2013.01); *A61M 5/3287* (2013.01); *A61M 2005/2026* (2013.01); *A61M 2005/3131* (2013.01); *A61M 2005/31508* (2013.01); *A61M 2005/31521* (2013.01); *A61M 2005/3247* (2013.01); *A61M 2005/3267* (2013.01)

(58) Field of Classification Search
CPC .......... A61M 5/31505; A61M 5/31565; A61M 5/31576; A61M 5/31578; A61M 5/31581; A61M 2005/31506
See application file for complete search history.

(56) References Cited

U.S. PATENT DOCUMENTS

| | | | |
|---|---|---|---|
| 2010/0010472 A1* | 1/2010 | Moore | A61M 5/31596 604/520 |
| 2011/0092915 A1 | 4/2011 | Olson et al. | |
| 2013/0018313 A1* | 1/2013 | Kramer | A61M 5/2033 604/131 |

FOREIGN PATENT DOCUMENTS

| | | | | |
|---|---|---|---|---|
| WO | WO 2011039216 A2 * | 4/2011 | ........ | A61M 5/31543 |
| WO | WO 2012000940 A2 * | 1/2012 | .......... | A61M 5/2033 |
| WO | WO-2012000940 A2 * | 1/2012 | .......... | A61M 5/2033 |
| WO | WO-2012/085026 A1 | 6/2012 | | |

* cited by examiner

LIQUID ADMINISTRATION DEVICE

CROSS-REFERENCE TO RELATED APPLICATIONS

This application is a continuation application filed under 35 U.S.C. § 111(a) claiming the benefit under 35 U.S.C. §§ 120 and 365(c) of PCT International Application No. PCT/JP2014/054909 filed on Feb. 27, 2014, which is based upon and claims the benefit of priority of Japanese Application No. 2013-047138 filed on Mar. 8, 2013, the entire contents of which are hereby incorporated by reference in their entireties.

BACKGROUND

Technical Field

The present disclosure relates to a liquid administration device.

Background Art

In the related art, a prefilled syringe is known which is aseptically filled with a drug solution and can administer the drug solution.

The prefilled syringe includes a syringe outer cylinder that has an opening part through which a drug solution is discharged; a needle tube that is provided in the opening part of the syringe outer cylinder and has a sharp needle tip at a distal end of the needle tube; a gasket that is slidable in the syringe outer cylinder; a drug solution with which a space surrounded by the syringe outer cylinder and the gasket is filled; and a plunger that is interlocked with the gasket on a proximal side and discharges the drug solution through the opening part by pressing the gasket toward the distal direction. When administering a drug solution using the prefilled syringe, the living body is punctured with the needle tube and a pressing operation of the plunger is performed while maintaining the punctured state. Accordingly, the drug solution is discharged from the gasket through the opening part, and therefore, it is possible to administer the drug solution to the living body through the needle tube.

However, in the prefilled syringe in the related art, for example, there is a problem in that the pressing resistance becomes high when administering a drug solution with high viscosity, and therefore, it is difficult to perform the pressing operation of the plunger. In addition, there is a problem in that the pressing operation of the plunger is difficult when a person with a weak amount of force, rheumatism patients who have a pain or deformation in the fingers, and the like perform self administration, even with a drug solution having a low viscosity.

U.S. Patent Publication No. 2011/0092915A discloses a liquid administration device which is constituted such that a plunger is pressed in a distal direction due to biasing force of a coil spring and automatically moves in the distal direction, when administering a drug solution into a living body. According to the liquid administration device, it is possible to easily and reliably administer a drug solution even with a relatively high viscosity and to easily and reliably administer a drug solution even by a person with a weak amount of force, a patient with rheumatism who has a pain or deformation in the fingers, and the like.

However, at the time of administering a drug solution to a living body, in some cases, it is necessary to temporarily suspend the administration for reasons such as weakening of pain due to the drug solution.

However, in the liquid administration device according to U.S. Patent Publication No. 2011/0092915A, it is structurally impossible to temporarily stop the plunger, and therefore, it is impossible to temporarily suspend the administration of a drug solution.

SUMMARY

An object of certain embodiments of the present invention is to provide a liquid administration device with which it is possible to prevent a liquid from being discharged through a distal end of a needle tube when suspending administration of the liquid.

In one embodiment, a liquid administration device includes: a structure that includes: a cylindrical body including a bottom part in a distal portion and an opening in a proximal portion, the cylindrical body being fillable with a liquid, a needle tube positioned in the distal portion of the cylindrical body, the needle tube having a sharp needle tip at a distal end, wherein a proximal end of the needle tube is communicable with the inside of the cylindrical body, and a gasket installed in the cylindrical body, the gasket being slidable in an axial direction of the cylindrical body; an operation member configured to perform a pressing operation by pressing the gasket such that the liquid is discharged from the needle tube; a pressing mechanism configured to generate a pressing force for pressing the gasket; and a pressing force transmission inhibiting mechanism configured to inhibit transmission of the pressing force to the gasket during the pressing operation.

In one aspect, the pressing force transmission inhibiting mechanism is configured to inhibit the transmission of the pressing force by rotation of at least one of the operation member and the structure around a central axis.

In one aspect, the pressing force transmission inhibiting mechanism includes: a first engagement portion provided in one of the structure and the operation member, and a second engagement portion provided in the other one of the structure and the operation member. The pressing force transmission inhibiting mechanism is placeable in an engagement state in which the transmission of the pressing force to the gasket is inhibited due to the engagement between the first engagement portion and the second engagement portion, and a released state in which the pressing force is transmitted to the gasket by release of the engagement state, during the pressing operation. The liquid administration device further includes a rotary mechanism configured to allow for selection between the engagement state and the released state, by relative rotation of the first engagement portion and the second engagement portion around a central axis of the structure.

In one aspect, in the engagement state, a positional relationship between the structure and the operation member in the central axis direction of the structure is fixed, and accordingly, the transmission of the pressing force to the gasket is inhibited.

In one aspect, the second engagement portion is engageable with the first engagement portion at a plurality of locations in an axial direction of the operation member.

In one aspect, the first engagement portion has a convex portion which is provided in one of the structure and the operation member. The second engagement portion has a plurality of concave portions which are provided in parallel along an axial direction of the other one of the structure and the operation member and are engageable with the convex portion. In the engagement state, the convex portion and at least one of the concave portions are engaged with each other, a positional relationship between the structure and the operation member in a central axis direction of the structure is fixed, and accordingly, the transmission of the pressing force to the gasket is inhibited.

In one aspect, at least one of the first engagement portion and the second engagement portion is provided in the plunger of the operation member. The operation member includes an outer cylinder that is disposed outside the structure. The rotary portion includes: an inclined rail portion provided in the outer cylinder, and a slider portion provided in the plunger, the slider portion being movable along the rail. The plunger is configured so as to relatively rotate around the central axis with respect to the outer cylinder by the slider portion moving relative to the outer cylinder along the rail portion.

In one aspect, the liquid is a drug solution.

In one aspect, the pressing mechanism comprising at least one coil spring.

According to certain embodiments of the present invention, it is possible to prevent a liquid from being discharged from a distal end of a needle tube when temporarily suspending administration of the liquid, because the present invention has a pressing force transmission inhibiting portion. In addition, it is possible to restart the administration of the liquid which is once suspended. Accordingly, it is possible to prevent the liquid from being wasteful or insufficient, and to administer a sufficient amount of the liquid to a living body.

DETAILED DESCRIPTION

Hereinafter, a liquid administration device of embodiments of the present invention will be described in detail based on the preferred embodiment shown in the accompanying drawings.

First Embodiment

Figure 1:
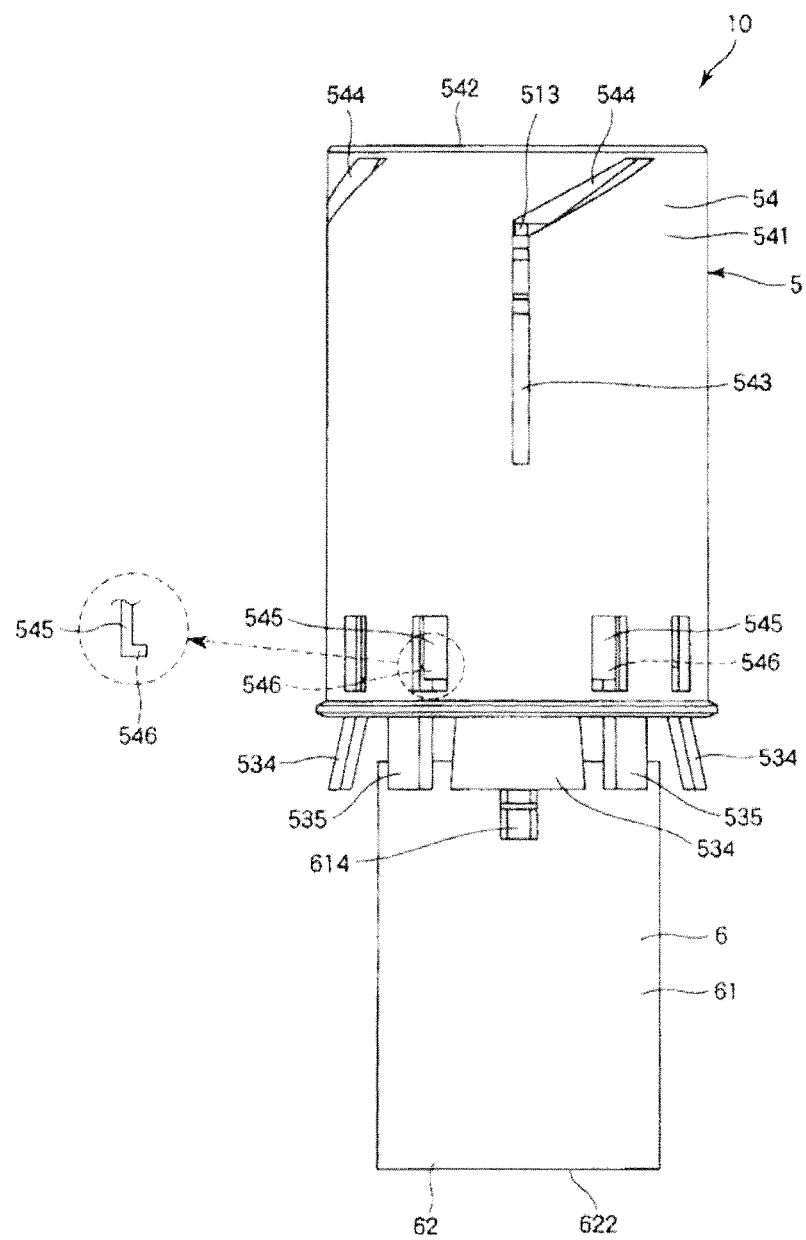
FIG. 1 is a side view showing a first embodiment of a liquid administration device of the present invention.
Figure 2:
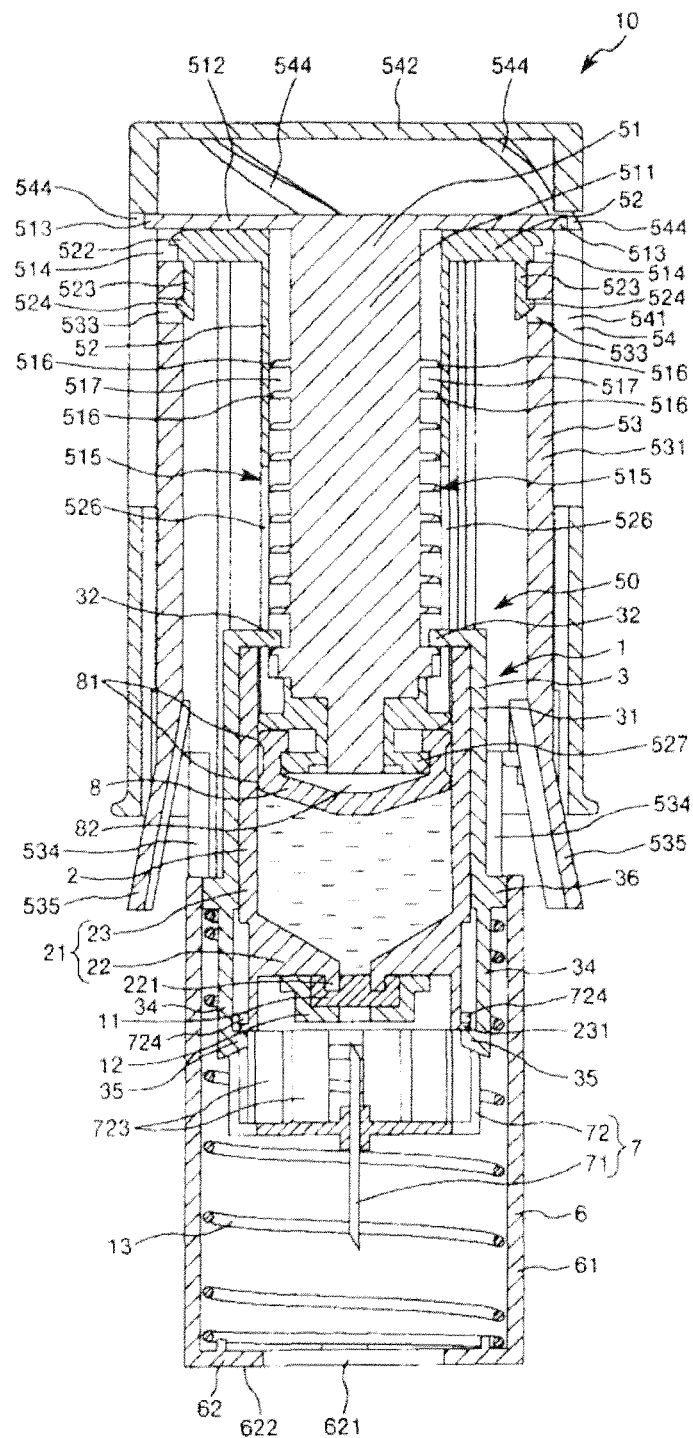
FIG. 2 is a longitudinal sectional view of the liquid administration device shown in FIG. 1.
Figure 3:
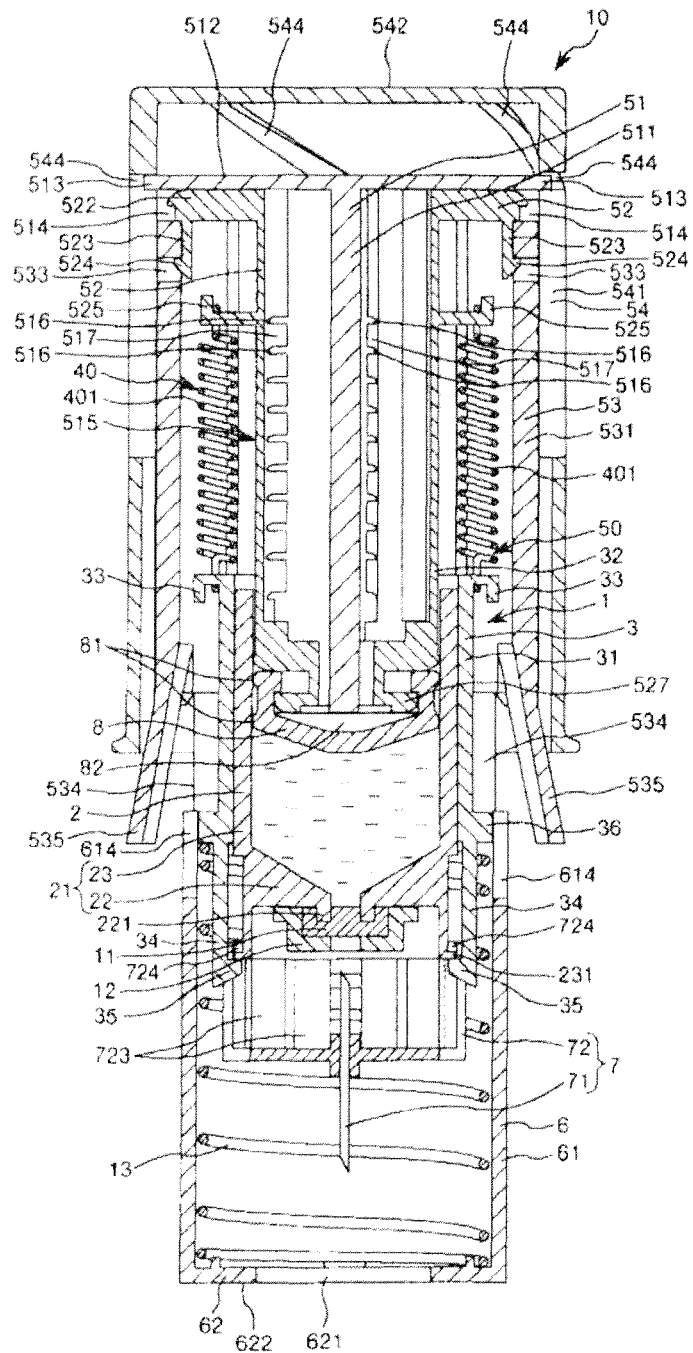
FIG. 3 is a longitudinal sectional view in which the liquid administration device shown in FIGS. 1 and 2 is rotated by 90°.
Figure 4:
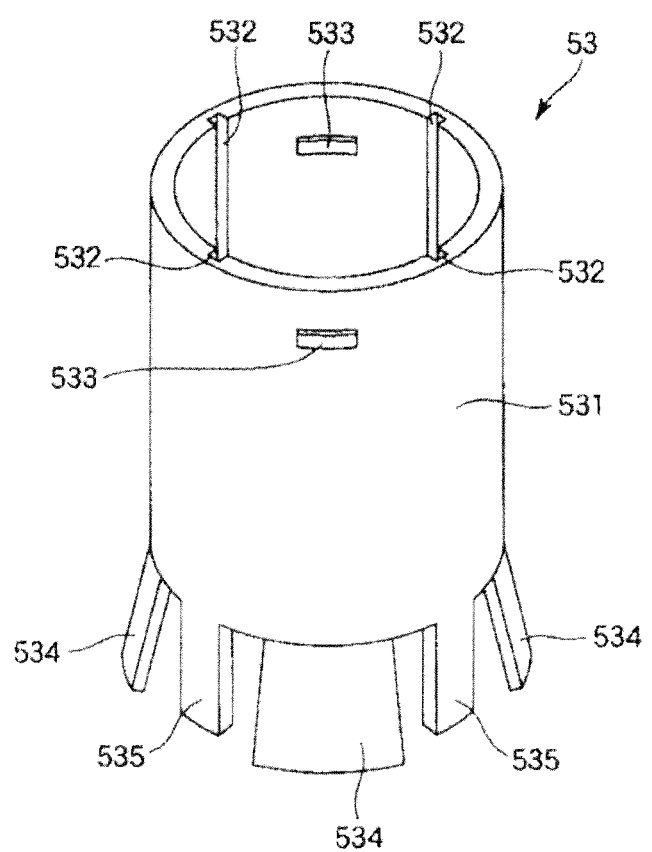
FIG. 4 is a perspective view of an inner main body of an operation member of the liquid administration device shown in FIG. 1.
Figure 5:
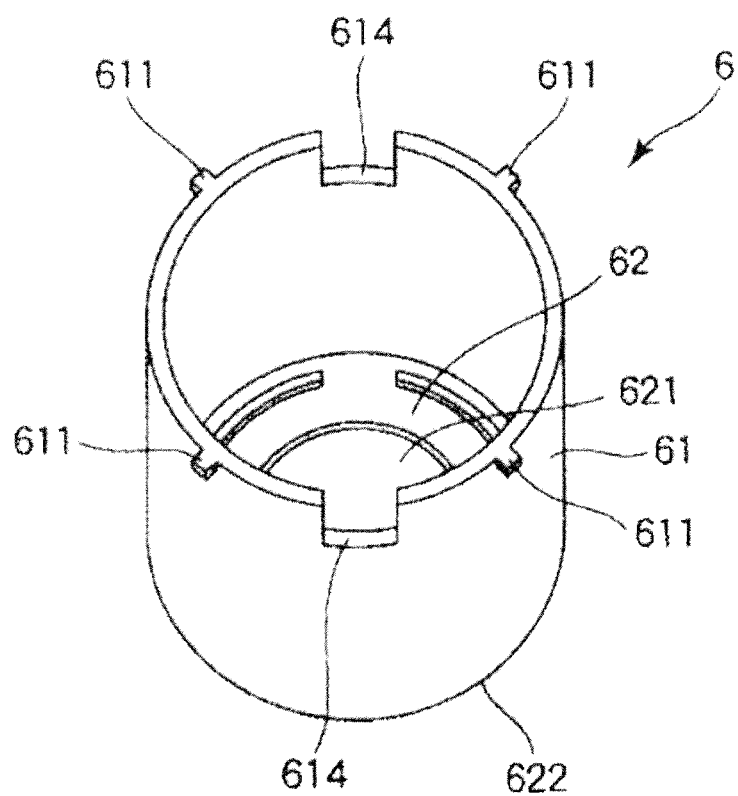
FIG. 5 is a perspective view of a cover member of the liquid administration device shown in FIG. 1.
Figure 6:
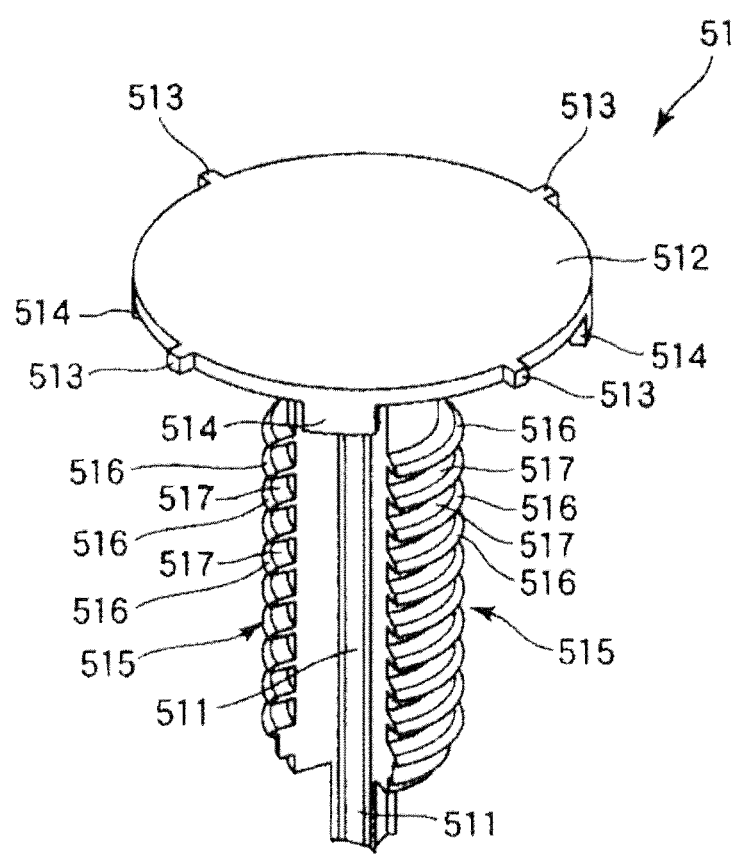
FIG. 6 is a perspective view of an inner plunger of the operation member of the liquid administration device shown in FIG. 1.
Figure 7:
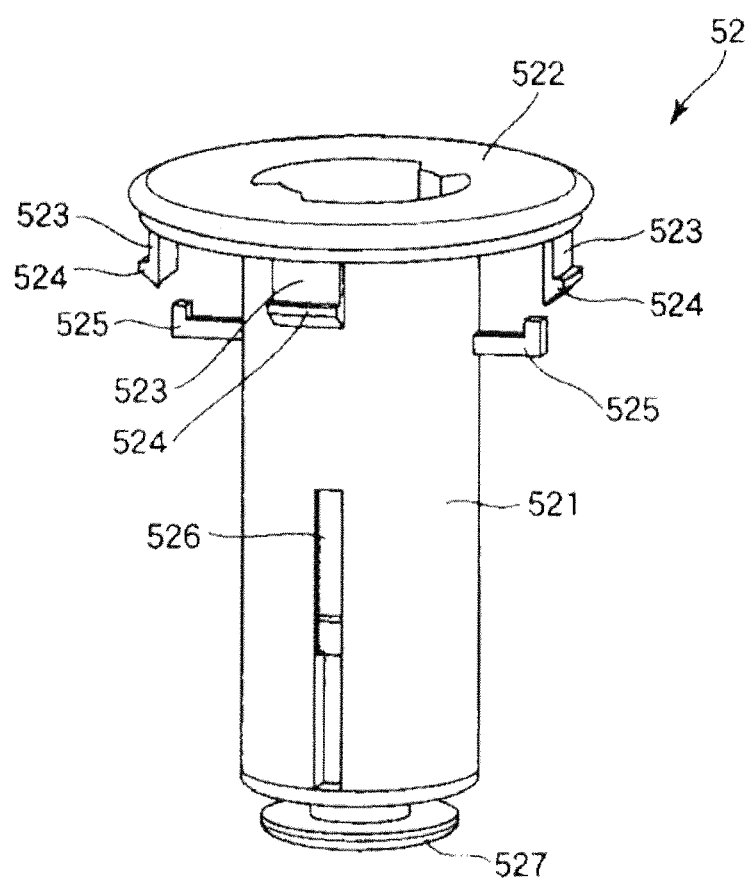
FIG. 7 is a perspective view of an outer plunger of the operation member of the liquid administration device shown in FIG. 1.
Figure 8:
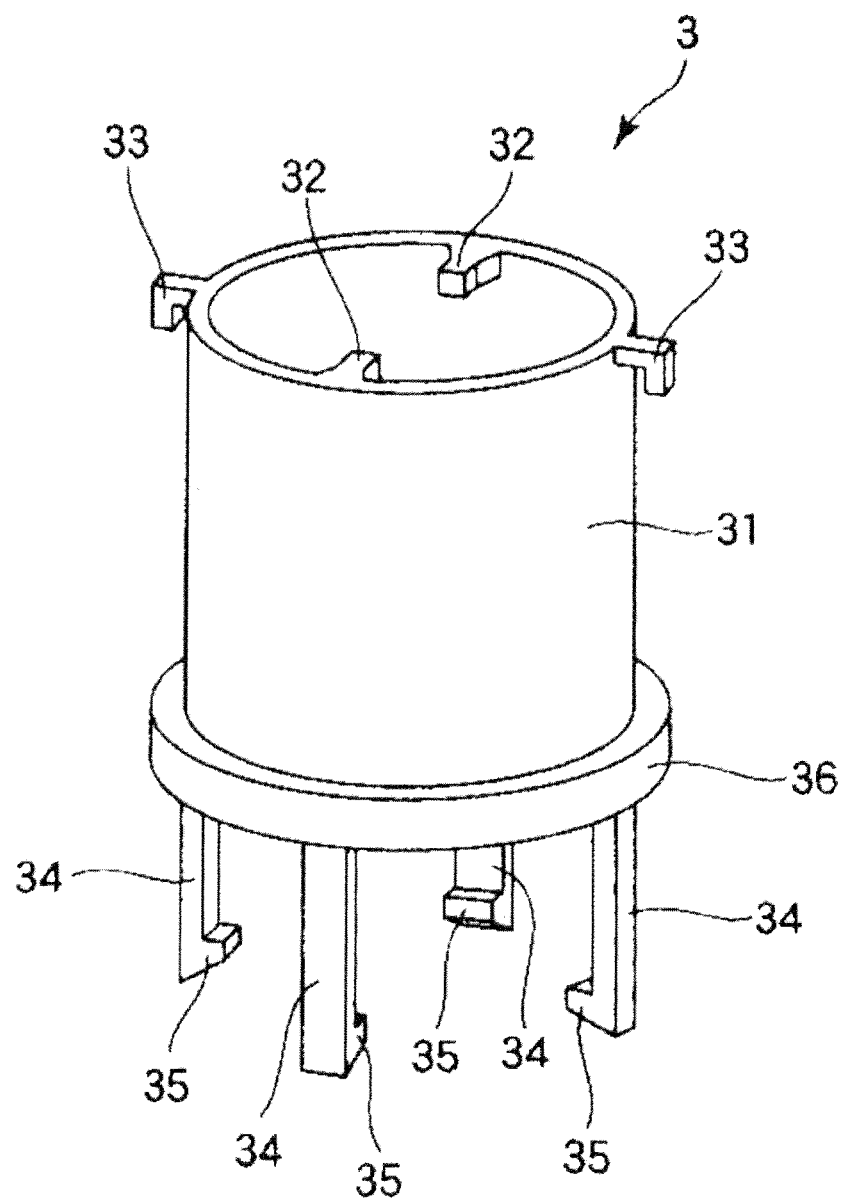
FIG. 8 is a perspective view of an administration restricting member of a structure of the liquid administration device shown in FIG. 1.
Figure 9:
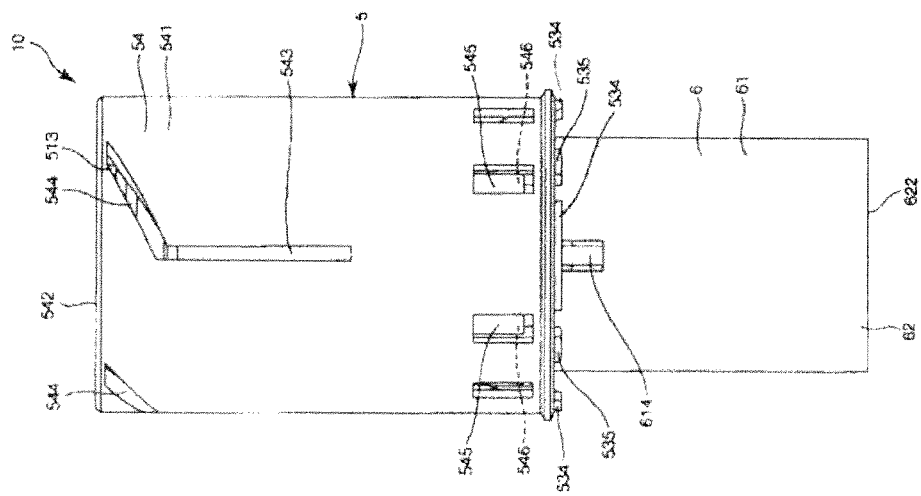
FIG. 9 is a side view showing an operation state in use of the liquid administration device shown in FIG. 1 in order.
Figure 10:
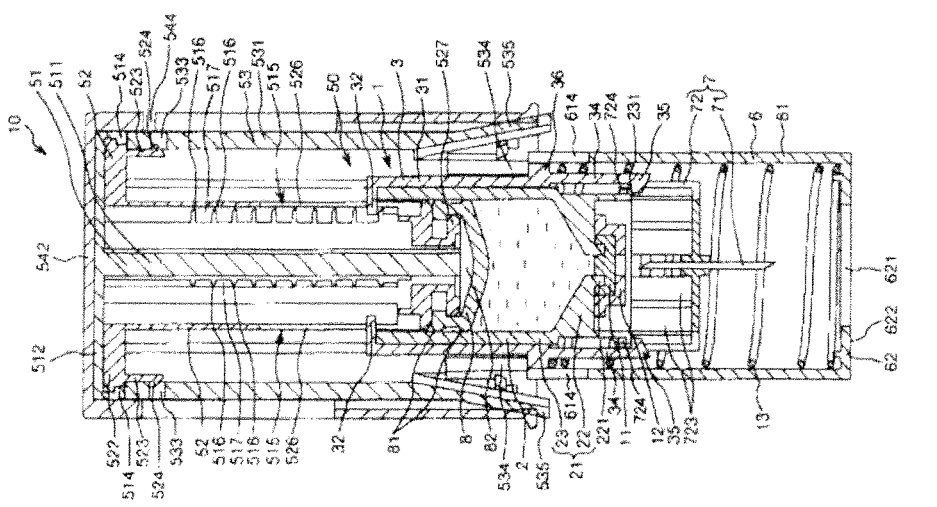
FIG. 10 is a longitudinal sectional view showing the operation state in use of the liquid administration device shown in FIG. 1 in order.
Figure 11:
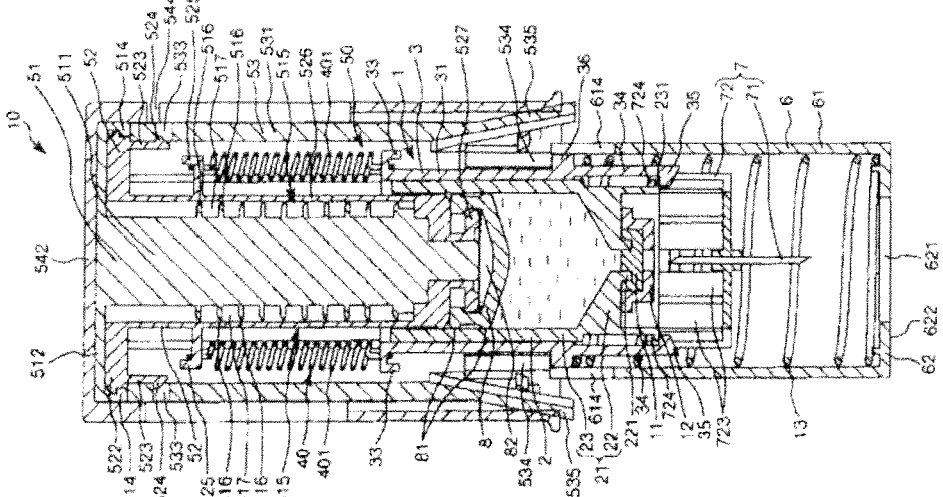
FIG. 11 is a view showing the operation state in use of the liquid administration device shown in FIG. 1 in order, and is a longitudinal sectional view when the liquid administration device shown in FIGS. 9 and 10 is rotated by 90°.
Figure 12:
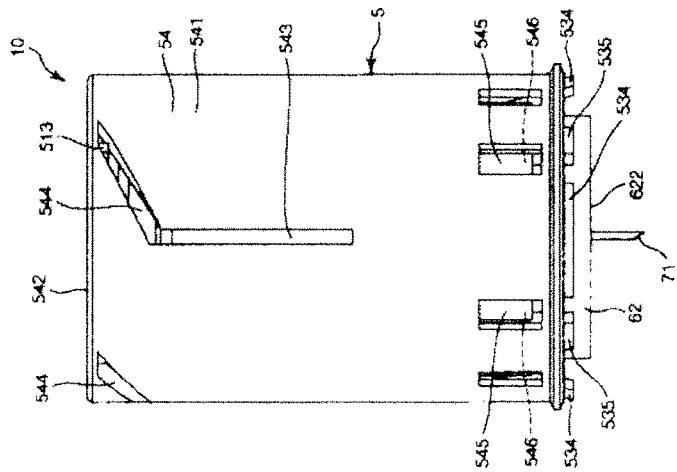
FIG. 12 is a side view showing the operation state in use of the liquid administration device shown in FIG. 1 in order.
Figure 13:
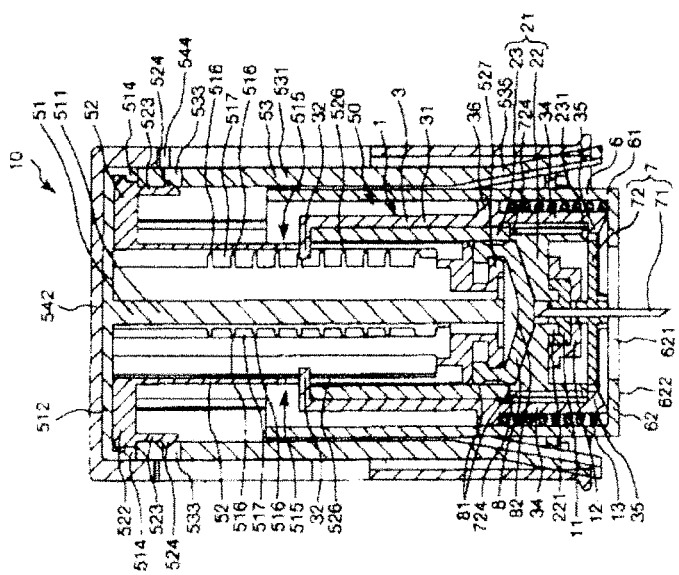
FIG. 13 is a longitudinal sectional view showing the operation state in use of the liquid administration device shown in FIG. 1 in order.
Figure 14:
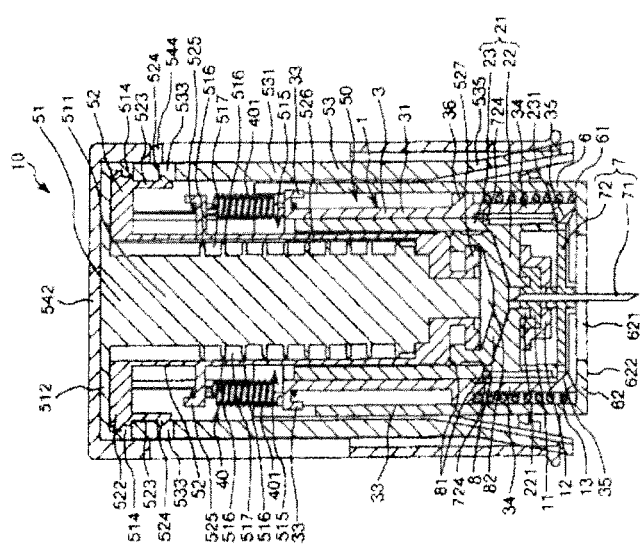
FIG. 14 is a view showing the operation state in use of the liquid administration device shown in FIG. 1 in order, and is a longitudinal sectional view when the liquid administration device shown in FIGS. 12 and 13 is rotated by 90°.
Figure 15:
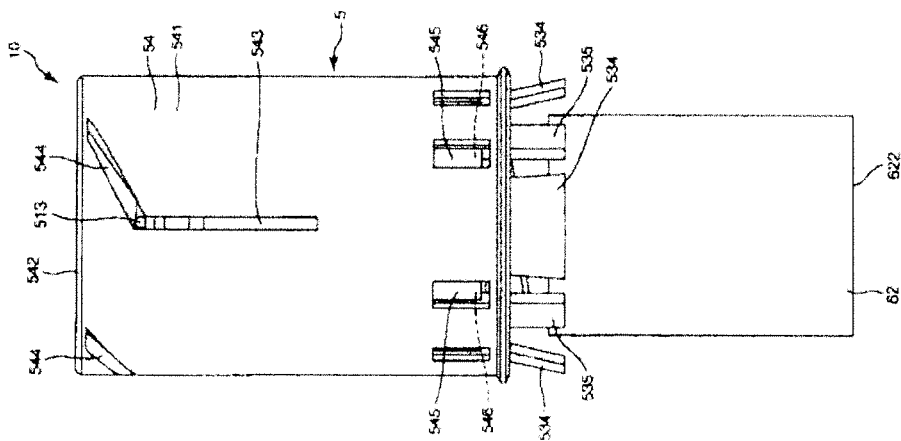
FIG. 15 is a side view showing the operation state in use of the liquid administration device shown in FIG. 1 in order.
Figure 16:
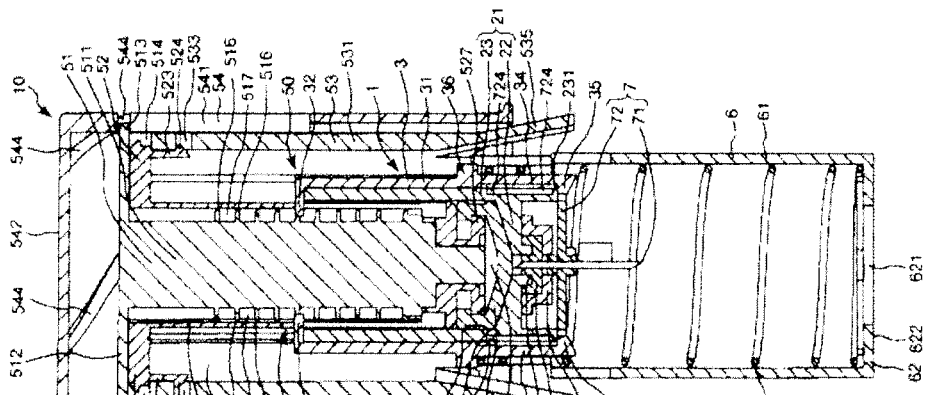
FIG. 16 is a longitudinal sectional view showing the operation state in use of the liquid administration device shown in FIG. 1 in order.
Figure 17:
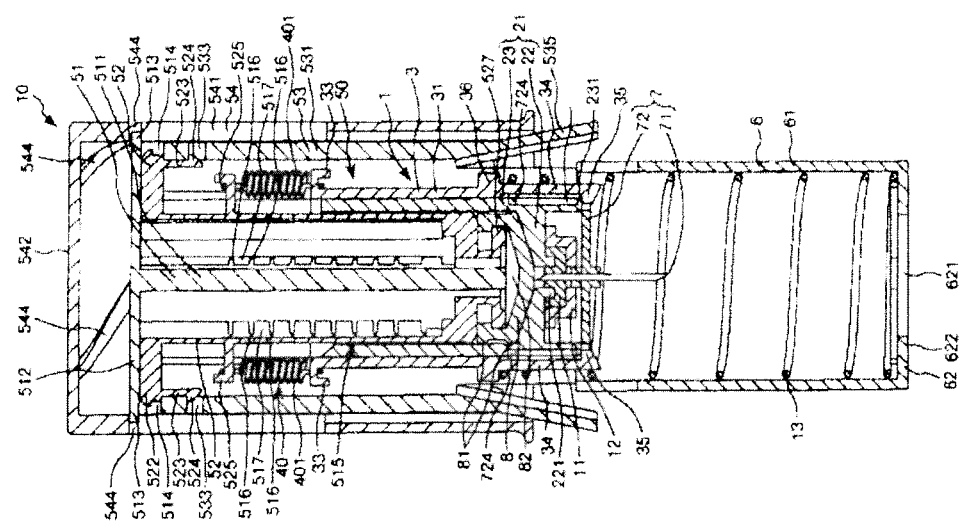
FIG. 17 is a view showing the operation state in use of the liquid administration device shown in FIG. 1 in order, and is a longitudinal sectional view when the liquid administration device shown in FIGS. 15 and 16 is rotated by 90°.
Figure 18:
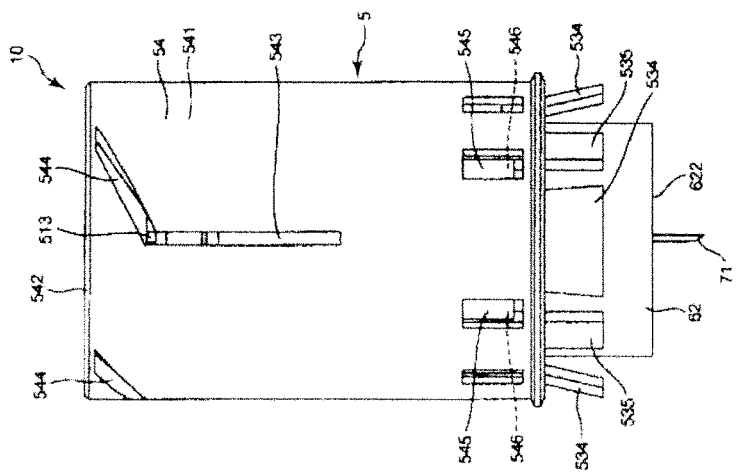
FIG. 18 is a side view showing the operation state in use of the liquid administration device shown in FIG. 1 in order.
Figure 19:
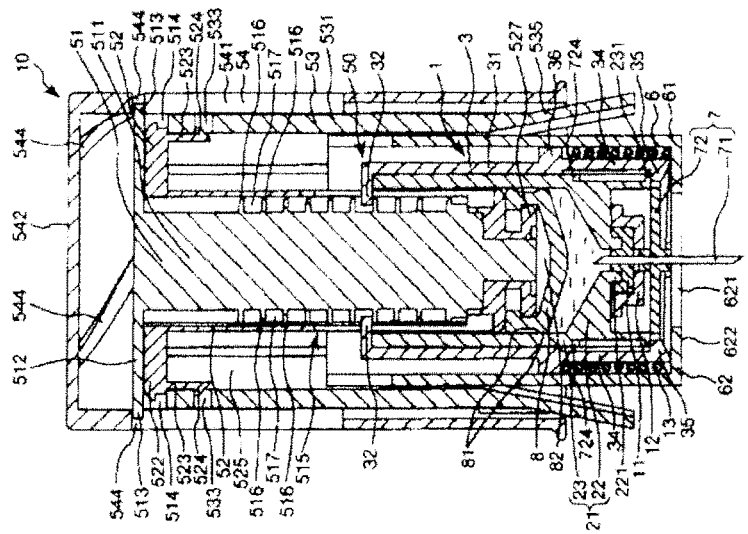
FIG. 19 is a longitudinal sectional view showing the operation state in use of the liquid administration device shown in FIG. 1 in order.
Figure 20:
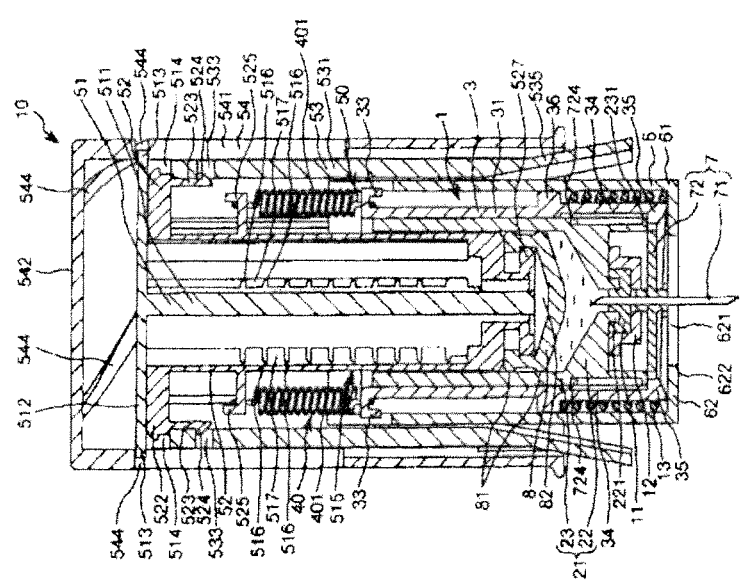
FIG. 20 is a view showing the operation state in use of the liquid administration device shown in FIG. 1 in order, and is a longitudinal sectional view when the liquid administration device shown in FIGS. 18 and 19 is rotated by 90°.

FIG. 1 is a side view showing a first embodiment of a liquid administration device of the present invention. FIG. 2 is a longitudinal sectional view of the liquid administration device shown in FIG. 1. FIG. 3 is a longitudinal sectional view in which the liquid administration device shown in FIGS. 1 and 2 is rotated by 90°. FIG. 4 is a perspective view of an inner main body of an operation member of the liquid administration device shown in FIG. 1. FIG. 5 is a perspective view of a cover member of the liquid administration device shown in FIG. 1. FIG. 6 is a perspective view of an inner plunger of the operation member of the liquid administration device shown in FIG. 1. FIG. 7 is a perspective view of an outer plunger of the operation member of the liquid administration device shown in FIG. 1. FIG. 8 is a perspective view of an administration restricting member of the structure of the liquid administration device shown in FIG. 1. FIG. 9 is a side view showing an operation state in use of the liquid administration device shown in FIG. 1 in order. FIG. 10 is a longitudinal sectional view showing the operation state in use of the liquid administration device shown in FIG. 1 in order. FIG. 11 is a view showing the operation state in use of the liquid administration device shown in FIG. 1 in order, and is a longitudinal sectional view when the liquid administration device shown in FIGS. 9 and 10 is rotated by 90°. FIG. 12 is a side view showing the operation state in use of the liquid administration device shown in FIG. 1 in order. FIG. 13 is a longitudinal sectional view showing the operation state in use of the liquid administration device shown in FIG. 1 in order. FIG. 14 is a view showing the operation state in use of the liquid administration device shown in FIG. 1 in order, and is a longitudinal sectional view when the liquid administration device shown in FIGS. 12 and 13 is rotated by 90°. FIG. 15 is a side view showing the operation state in use of the liquid administration device shown in FIG. 1 in order. FIG. 16 is a longitudinal sectional view showing the operation state in use of the liquid administration device shown in FIG. 1 in order. FIG. 17 is a view showing the operation state in use of the liquid administration device shown in FIG. 1 in order, and is a longitudinal sectional view when the liquid administration device shown in FIGS. 15 and 16 is rotated by 90°. FIG. 18 is a side view showing the operation state in use of the liquid administration device shown in FIG. 1 in order. FIG. 19 is a longitudinal sectional view showing the operation state in use of the liquid administration device shown in FIG. 1 in order. FIG. 20 is a view showing the operation state in use of the liquid administration device shown in FIG. 1 in order, and is a longitudinal sectional view when the liquid administration device shown in FIGS. 18 and 19 is rotated by 90°. Note that, hereinafter, the upper side is described as "proximal end (rear end)" or "upper (upward)", the lower side is described as "distal end" or "lower (downward)", and the vertical direction is described as "axial direction" or "longitudinal direction" in FIGS. 1 to 20. In addition, FIG. 1 also shows a side view of a portion that is surrounded by a dotted line (circle).

A liquid administration device 10 shown in FIGS. 1 to 3 and 9 to 20 is a medical device that is used when administering (injecting) a liquid to a living body. Note that the liquid is appropriately selected according to its purpose of use, and examples thereof include drug solutions, which are mainly injected hypodermically, such as hematopoietic agents, vaccines, hormone preparations, antirheumatic agents, anticancer agents, anesthetics, and anticoagulants.

The liquid administration device 10 includes a structure 1; an operation member 5; a cover member 6 that is disposed on an outer peripheral side of the structure 1; a coil spring 13 that is a first biasing member for biasing the cover member 6 in the distal direction; a pressing mechanism (pressing portion) 40; and a pressing force transmission inhibiting mechanism (pressing force transmission inhibiting portion) 50.

As shown in FIGS. 2 and 3, the structure 1 includes a cylindrical body 2; an administration restricting member (administration regulating portion) 3; a puncture needle 7 that is configured to have a double ended needle (needle tube) 71 and a support member 72; and a gasket 8 that is installed in the cylindrical body 2 and is slidable along the axial direction of the cylindrical body 2.

As shown in FIGS. 2 and 3, the cylindrical body 2 has a cylindrical main body 21. The cylindrical main body 21 is configured to have a member that has a bottom part 22 in a distal portion; a side wall 23 that is erected from the edge of the bottom part 22; and an opening portion in a proximal portion, that is, a member forming a bottomed cylindrical shape. The inside of the cylindrical body 2 can be filled with a liquid.

The bottom part 22 of the cylindrical main body 21 forms a mortar shape and an opening part 221, through which a liquid passes, penetrates in its central portion and opens. The diameter of the opening part 221 is decreased with respect to a portion of the side wall 23 of the cylindrical main body 21. A liquid is absorbed or discharged from the opening part 221.

In addition, a distal portion of the side wall 23 of the cylindrical main body 21 is positioned further on a distal side of the bottom part 22, and a rib 231 is formed over a one turn in an outer peripheral portion of the distal portion of the side wall 23.

In addition, the cylindrical body 2 has a sealing member (sealing portion) 11 that liquid-tightly seals the opening part 221 of the cylindrical main body 21; and a fixing member 12 that fixes the sealing member 11 from its distal side. Such a cylindrical body 2 is disposed inside the administration restricting member 3 and is supported by the administration restricting member 3.

The sealing member 11 is an elastic body, and an annular groove is formed on its proximal surface. The opening part 221 is liquid-tightly sealed by fitting the opening part 221 of the cylindrical main body 21 into the groove.

The fixing member 12 is a cylindrical member. The fixing member 12 is attached to the sealing member 11 from proximal ends and outer peripheral sides of the sealing member 11 and the opening part 221 and fixes the sealing member 11 to the bottom part 22. Accordingly, removal of the sealing member 11 from the cylindrical main body 21 is reliably prevented. Note that the method of fixing the fixing member 12 is not particularly limited, and examples thereof include adhesion using adhesives, solvents, or the like; and weldings such as heat-welding, high frequency welding, and ultrasonic welding.

As shown in FIG. 8, the administration restricting member 3 has a main body portion 31 that forms a cylindrical shape. A pair of spurs (convex portions) 32 that are disposed so as to face each other is protrusively formed in an inner peripheral portion of the proximal portion of the main body portion 31 toward a central axis (inside) of the main body portion 31. Note that a first engagement portion of the pressing force transmission inhibiting mechanism 50 is formed by the spurs 32.

In addition, a pair of hooks 33 that are disposed so as to face each other is protrusively formed in an outer peripheral portion of the proximal portion of the main body portion 31 toward the central axis of the main body portion 31. The shape of each hook 33 is not particularly limited, but in the configuration of the drawing, the shape thereof forms an L shape. Note that each hook 33 and each spur 32 are mutually disposed at substantially equiangular intervals along the circumferential direction of the main body portion 31 when seen from the axial direction of the main body portion 31.

In addition, four elastic arm portions 34 are protrusively formed in the distal portion of the main body portion 31 in the distal direction. The arm portions 34 are disposed at substantially equiangular intervals along the circumferential direction of the main body portion 31. Each claw 35 that inwardly protrudes is formed in the distal portion of each arm portion 34. Each claw 35 is engaged with the distal side of the rib 231 of the cylindrical body 2 and each spur 32 is engaged with the proximal end of the cylindrical body 2, and accordingly, the administration restricting member 3 and the cylindrical body 2 are interlocked with each other.

In addition, a rib 36 is formed over one turn in the outer peripheral portion of the distal portion of the main body portion 31.

Note that the administration restricting member 3 is relatively movable to the operation member 5 in the axial direction, together with the cylindrical body 2.

In addition, constituent materials for the cylindrical main body 21, the administration restricting member 3, the fixing member 12, the cover member 6, the support member 72, and the operation member 5 are not particularly limited, and examples thereof include various types of resins such as polyvinyl chloride, polyethylene, polypropylene, cyclic polyolefin, polystyrene, poly-(4-methylpentene-1), polycarbonate, acrylic resins, acrylonitrile-butadiene-styrene copolymers, polyesters such as polyethylene terephthalate and polyethylene naphthalate, butadiene-styrene copolymers, and polyamides (for example, nylon 6, nylon 6-6, nylon 6-10 and nylon 12). Among these, resins such as polypropylene, cyclic polyolefin, polyesters and poly-(4-methylpentene-1) are preferable in view of the ease in molding.

In addition, elastic materials constituting the sealing member 11 and the gasket 8 are not particularly limited, and examples thereof include elastic materials such as various rubber materials such as natural rubber, butyl rubber, isoprene rubber, butadiene rubber, styrene-butadiene rubber, and silicone rubber; various types of thermoplastic elastomers, such as polyurethane, polyester, polyamide, olefin, and styrene elastomers; or mixtures thereof.

As shown in FIGS. 2 and 3, the puncture needle 7 is disposed in the distal portion of the cylindrical body 2. The puncture needle 7 is configured to have the double ended needle 71 and the support member 72 that supports and fixes the double ended needle 71.

The double ended needle 71 is a hollow needle tube, and has a sharp distal side needle tip at a distal end and also has a sharp proximal side needle tip at a proximal end. The double ended needle 71 can puncture a living body with the distal side needle tip and can pierce the sealing member 11 of the cylindrical body 2 with the proximal side needle tip.

A lumen part (hollow part) of the double ended needle 71 communicates with the cylindrical body 2 in a state where the sealing member 11 of the cylindrical body 2 is pierced with the proximal side needle tip, and functions as a flow path through which a liquid from the cylindrical body 2 passes.

The sealing member 11 of the cylindrical body 2 is pierced with the proximal side needle tip and the liquid is injected into the living body through the flow path of the double ended needle 71 after the living body is punctured to a predetermined depth from the skin using the distal side needle tip of the double ended needle 71.

Note that the constituent materials of the double ended needle 71 are not particularly limited, and examples thereof include metallic materials such as stainless steel, aluminum or aluminum alloys, and titanium or titanium alloys.

The double ended needle 71 having such a configuration is mounted in the distal portion of the cylindrical body 2 through the support member 72 so as to be movable along the axial direction of the cylindrical body 2. The support member 72 supports the double ended needle 71 with respect to the cylindrical body 2 so as to be movable along the axial direction thereof. The support member 72 forms a bottomed cylindrical shape. The double ended needle 71 is supported by and fixed to the bottom part of the support member 72 in a middle part of the double ended needle.

In addition, a plurality of elongated holes, which extend in the axial direction of the support member 72 and are opened in the proximal direction, are formed on the side wall of the support member 72, and accordingly, a plurality of protruding pieces 723 are formed on the side wall of the support member 72. Accordingly, it is possible to decrease or enlarge the diameter of the portion on the proximal side of the support member 72 by elastic deformation.

In addition, a rib 724 is formed in an inner peripheral portion of the proximal portion of each protruding piece 723 of the support member 72. Each rib 724 is engaged with the rib 231 of the cylindrical body 2 on the proximal side, and therefore, it is possible to prevent the puncture needle 7 from being separated from the distal portion of the cylindrical body 2.

In addition, each arm portion 34 of the administration restricting member 3 is positioned between two protruding pieces 723, which are adjacent to each other, of the support member 72. Accordingly, the puncture needle 7 is prevented from rotating in the circumferential direction during puncturing. Accordingly, it is possible to prevent coring when the proximal side needle tip of the double ended needle 71 penetrates the sealing member 11.

As mentioned above, the puncture needle 7 is supported so as to be movable to the cylindrical body 2 along the axial direction through the support member 72. Accordingly, the puncture needle 7 can take a separation state where the proximal side needle tip of the double ended needle 71 is separated from the sealing member 11 of the cylindrical body 2 as shown in FIGS. 2 and 3, and a pierced state where the sealing member 11 is pierced with the proximal side needle tip of the double ended needle 71 as shown in FIGS. 13 and 14. Accordingly, unintentional leaking of a liquid from the double ended needle 71 is prevented until the puncture needle 7 enters the pierced state.

As shown in FIGS. 2 and 5, the cover member 6 is disposed on the outer peripheral side of the cylindrical body 2.

The cover member 6 is supported so as to be movable to an inner cylinder 53, to be described later, of the operation member 5 in the axial direction. Accordingly, a living body is punctured to a predetermined depth from the skin using the distal side needle tip of the double ended needle 71 after a distal surface 622 of the cover member 6 is brought into contact with the living body.

The cover member 6 has five steps (positions) to be described later from before use to after use. The five positions include a first position (position (A)) (refer to FIGS. 1 to 3) at which the cover member 6 protrudes further on the distal side than the distal side needle tip of the double ended needle 71 in a state before use; a second position (position (B)) (refer to FIGS. 12 and 14) at which the cover member 6 is retreated in the proximal direction from the first position and the distal side needle tip of the double ended needle 71 is exposed from the distal end of the cover member 6; and a third position (refer to FIGS. 15 and 17) at which the cover member 6 moves in the distal direction from the second position and protrudes further on the distal side than the distal side needle tip of the double ended needle 71, and a safety mechanism is operated after the completion of the administration.

Note that, in the present embodiment, when the cover member 6 is at the first position, the distal surface 622 of the cover member 6 protrudes further on the distal side than the distal side needle tip of the double ended needle 71 to cover the distal side needle tip of the double ended needle 71 using the cover member 6. Accordingly, the distal side needle tip of the double ended needle 71 is not exposed until the cover member 6 moves to the proximal side from the first position, and therefore, it is possible to prevent the skin of a user from being erroneously punctured with the distal side needle tip of the double ended needle 71 before the puncturing or the distal side needle tip from being damaged. In addition, when the cover member 6 is positioned at the second position, the distal side needle tip of the double ended needle 71 is exposed from the distal end of the cover member 6.

Note that, when the cover member 6 is at the first position, the aforementioned puncture needle 7 enters the separation state where the puncture needle is positioned further on the proximal side than the distal portion of the cover member 6. In contrast, when the cover member 6 moves to the second position, the cover member 6 presses and moves the double ended needle 71 (the double ended needle 71 together with the support member 72) toward the proximal direction, and the proximal side needle tip of the double ended needle 71 pierces the sealing member 11 of the cylindrical body 2 and the distal side needle tip of the double ended needle 71 punctures a living body. In addition, when the cover member 6 is at the second position, the sealing member 11 is pierced with the proximal side needle tip of the double ended needle 71, and the upper end surface inside the support member 72 and the distal surface of the cylindrical body 2 enter a state where they come into contact with each other.

The cover member 6 is configured to have a plate-shaped distal end wall part 62 that is disposed in the distal portion; and a side wall 61 that is erected in the proximal direction from the distal end wall part 62, that is, the cover member is configured to have a member that forms a bottomed cylindrical shape. In addition, the cover member 6 has a distal surface 622 at the distal end.

An opening 621 is formed at the central portion of the distal end wall part 62. As shown in FIGS. 12 to 14, when the cover member 6 is at the second position, the distal side needle tip of the double ended needle 71 protrudes (is exposed) from the opening 621.

As shown in FIG. 5, the side wall 61 forms a cylindrical shape. Four spurs 611 are protrusively formed on the outer peripheral surface of the proximal portion of the side wall 61 toward the outside. The spurs 611 are disposed at substantially equiangular intervals along the circumferential direction of the side wall 61. Each spur 611 is inserted into a groove 532 of the inner cylinder 53 to be described later and is movable along the groove 532. Accordingly, the cover member 6 becomes movable in the axial direction with respect to the inner cylinder 53.

A pair of cutout portions 614 that are disposed so as to face each other is formed in the proximal portion of the side wall 61. Each cutout portion 614 is disposed between two adjacent spurs 611, and in the configuration shown in the drawing, at an intermediate position between the two adjacent spurs 611. Note that each cutout portion 614 is disposed at a position that is the same as a hook 525 of an outer plunger 52, to be described later, in the axial direction, and accordingly, the cover member 6 and the hook 525 are designed not to interfere with each other when the cover member 6 moves.

As shown in FIGS. 2 and 3, a coil spring (compression coil spring) 13 is stored in the cover member 6 in a compressed state. The distal portion of the coil spring 13 is attached to the distal end wall part 62 inside the cover member 6, and the proximal portion of the coil spring 13 is attached to the rib 36 of the administration restricting member 3. In the compressed state in an unused state, the coil spring 13 is compressed by the weight loaded on the administration restricting member 3. Note that the coil spring 13 may not be compressed if the distal portion of the coil spring 13 is attached to the distal end wall part 62 inside the cover member 6 and the proximal portion of the coil spring 13 is attached to the rib 36 of the administration restricting member 3. For example, it is possible to bias the cover member 6 from the second position toward the first position (toward the distal direction) using the coil spring 13. With the biasing force of such a coil spring 13, the distal surface 622 of the cover member 6 can be made to protrude further on the distal side than the distal side needle tip of the double ended needle 71 until the liquid administration device 10 is completely used, and accordingly, it is possible to reliably prevent the erroneous puncturing due to the distal side needle tip.

Note that the constituent materials of the coil spring 13 are not particularly limited, and for example, metallic materials such as stainless steel can be used.

The gasket 8 is stored in the cylindrical body 2 so as to be slidable along the axial direction of the cylindrical body 2. Note that the space surrounded by the gasket 8 and the cylindrical body 2 is filled with a liquid in advance. The liquid in the cylindrical body 2 can be pushed out from the double ended needle 71 in a state where the double ended needle communicates with the cylindrical body 2, due to the gasket 8 moving toward the distal direction.

The outer shape of the gasket 8 is a flat or columnar shape, and two protruded parts 81 are formed in the outer peripheral part. Each protruded part 81 is separated along the axial direction of the gasket 8. In addition, each of protruded part 81 forms a ring shape along the circumferential direction of the gasket 8, and the outer diameter thereof is slightly larger than the inner diameter of the cylindrical body 2 in a natural state where external force is not applied. Accordingly, each of protruded part 81 can slide while being brought into close contact with the inner peripheral part of the cylindrical body 2, and thus, it is possible to reliably retain the liquid-tightness and improve slidability.

In addition, a concave portion 82, which interlocks an inner plunger 51 and the outer plunger 52 of the operation member 5, to be described later, by inserting (fitting) the inner plunger 51 and the outer plunger 52 therein, is opened on the proximal surface of the gasket 8.

As shown in FIGS. 1 to 3, the operation member 5 has the inner plunger 51 and the outer plunger 52 that interlock the gasket 8 on the proximal side and press the gasket 8 in the distal direction; the inner cylinder 53; and an outer cylinder 54. A plunger is constituted by the inner plunger 51 and the outer plunger 52. In addition, the inner plunger 51, the outer plunger 52, the inner cylinder 53, and the outer cylinder 54 are concentrically disposed in this order from the inside. In addition, the outer plunger 52 and the inner cylinder 53 are interlocked with each other. In addition, the inner cylinder 53 is movable only in the axial direction and is not rotatable around the axis, with respect to the outer cylinder 54. In addition, the inner plunger 51 is rotatable only around the axis and is not movable in the axial direction, with respect to the outer plunger 52. The operation member 5 is a member that performs pressing operation (discharging operation) to discharge a liquid in the cylindrical body 2 from the double ended needle 71 by moving the gasket 8 in the distal direction using the inner plunger 51 and the outer plunger 52 moving in the distal direction.

As shown in FIG. 6, the inner plunger 51 has a main body portion 511 having a longitudinal shape, that is, a rod shape; and a disk-shaped flange 512 that is provided at the proximal end of the main body portion 511. The inner plunger is installed so as to be freely rotatable (rotationally movable) around the axis of the outer plunger 52 in a state where the main body portion 511 of the inner plunger is inserted into the outer plunger 52.

Four spurs (slider portions) 513 are protrusively formed in the outer peripheral portion of the flange 512 toward the outside. The spurs 513 are disposed at substantially equiangular intervals along the circumferential direction of the flange 512.

In addition, four claws 514 are protrusively formed in the outer peripheral portion of the flange 512 toward the distal side. The claws 514 are disposed at substantially equiangular intervals along the circumferential direction of the flange 512. In addition, each claw 514 is disposed between two adjacent spurs 513, and in the configuration shown in the drawing, at an intermediate position between the two adjacent spurs 513. Each claw 514 is engaged with the flange 522 of the outer plunger 52, and accordingly, the movement of the inner plunger 51 in the axial direction is inhibited, but the inner plunger 51 is rotatable around the axis, with respect to the outer plunger 52.

In addition, a pair of rib rows 515 that are disposed so as to face each other when seen in a plan view is formed in the outer peripheral portion of the main body portion 511. The rib rows 515 are respectively formed by a plurality of ribs 516. Each rib 516 extends in the circumferential direction of the main body portion 511 and is formed in a part of the main body portion 511 in the circumferential direction when seen in a plan view.

In addition, the ribs 516 of the rib rows 515 are arranged in parallel at substantially equal intervals along the axial direction of the main body portion 511. In other words, a concave portion 517 is formed by two adjacent ribs 516 therebetween in each rib row 515 and a plurality of concave portions 517 are arranged in parallel at substantially equal intervals along the axial direction of the main body portion 511. Note that a second engagement portion of the pressing force transmission inhibiting mechanism 50 is formed by the rib rows 515.

As shown in FIG. 7, the outer plunger 52 has a main body portion 521 having a cylindrical shape; and a disk-shaped flange 522 that is provided at the proximal end of the main body portion 521. An opening that communicates with the lumen of the main body portion 521 is formed in the flange 522.

In addition, four elastic arm portions 523 are protrusively formed on the distal side of the outer peripheral portion of the flange 522 in the distal direction. The arm portions 523 are disposed at substantially equiangular intervals along the circumferential direction of the flange 522. Each claw 524 that outwardly protrudes is formed in the distal portion of each arm portion 523. Each claw 524 is engaged with each of hole portions 533 by being inserted into each hole portion 533 to be described later from the inside on the proximal side of the inner cylinder 53 and the outer plunger 52 and the inner cylinder 53 are interlocked with each other.

Note that the method of interlocking the outer plunger 52 and the inner cylinder 53 is not limited thereto, and examples thereof include adhesion using adhesives, solvents, or the like; and weldings such as heat-welding, high frequency welding, and ultrasonic welding.

In addition, a pair of hooks 525 that are disposed so as to face each other is protrusively formed in the outer peripheral portion of the proximal portion of the main body portion 521 of the outer plunger 52 toward the outside. The shape of each hook 525 is not particularly limited, but in the configuration of the drawing, the shape thereof forms an L shape.

In addition, a pair of elongated holes 526 that are disposed so as to face each other is formed in the main body portion 521 over the distal portion from the central portion of the main body portion. Each elongated hole 526 extends along the axial direction. The main body portion 521 of the outer plunger 52 is inserted into the administration restricting member 3 and each spur 32 of the administration restricting member 3 is inserted into each elongated hole 526. Accordingly, the administration restricting member 3 can relatively move to the outer plunger 52 and the inner plunger 51 in the axial direction. In addition, the rotation of the administration restricting member 3 around the axis with respect to the outer plunger 52 is inhibited.

In addition, an interlock portion 527 that is inserted into the concave portion 82 of the gasket 8 is formed in the distal portion of the main body portion 521. The outer plunger 52 (operation member 5) and the gasket 8 are interlocked by the interlock portion 527 being inserted into the concave portion 82 of the gasket 8. Note that the method of fixing the gasket 8 to the main body portion 521 is not particularly limited thereto, and other examples thereof include a method of forming a male screw on the main body portion 521, forming a female screw, which is screwed into the male screw, on the gasket 8, and screwing both the screws together. Note that, in the present example, the operation member 5 is interlocked to the gasket 8 on the proximal side, but may not be interlocked therewith.

As shown in FIG. 4, the inner cylinder 53 has a cylindrical main body 531 that forms a cylindrical shape.

Four grooves 531 are formed on the inner peripheral surface of the cylindrical main body 531 (refer to FIG. 2). Grooves 532 extend along the axial direction thereof and are arranged in parallel at equiangular intervals along the circumferential direction. In addition, each groove 53 opens at the proximal end of the cylindrical main body 531. In addition, the distal side of each groove 53 is blocked. Accordingly, the cover member 6 can be inhibited from being separated from the distal side of the inner cylinder 53.

In addition, a pair of hole portions 533 that are disposed so as to face each other is formed in the proximal portion of the cylindrical main body 531. Each hole portion 533 is disposed between two adjacent grooves 532, and in the configuration shown in the drawing, at an intermediate position between the two adjacent grooves 532.

In addition, four elastic protruding pieces (biasing mechanisms) 534 are protrusively formed at the distal end of the cylindrical main body 531 toward the distal side. The protruding pieces 534 are disposed at substantially equiangular intervals along the circumferential direction of the cylindrical main body 531. In addition, the distal portion of each protruding piece 534 is positioned further on the outer peripheral side than the proximal portion. Note that a biasing mechanism (biasing portion), which biases the outer cylinder 54 with respect to the inner plunger 51 (plunger) toward the proximal direction, is formed by these protruding pieces 534.

In addition, four elastic protruding pieces 534 are protrusively formed at the distal end of the cylindrical main body 531 toward the distal side. The protruding pieces 534 are disposed at substantially equiangular intervals along the circumferential direction of the cylindrical main body 531. In addition, each protruding piece 534 is disposed between two adjacent protruding pieces 534.

As shown in FIGS. 1 to 3, the outer cylinder 54 is disposed on the proximal side and the outer peripheral side of the inner plunger 51, the outer plunger 52, and the inner cylinder 53.

The outer cylinder 54 is configured to have a plate-shaped proximal end wall part 542 that is disposed in the proximal portion; and a side wall 541 that is erected in the distal direction from the proximal end wall part 542, that is, the outer cylinder is configured to have a member that forms a bottomed cylindrical shape. The outer cylinder 54 functions as a grip portion when gripping the operation member 5.

In addition, four inclined grooves (cam grooves) 544, as inclined rail portions, and four linear grooves 543 into which the four spurs 513 of the inner plunger 51 are inserted are formed on the inner peripheral surface of the side wall 541 of the outer cylinder 54. The spurs 513 relatively move along the inclined grooves 544. In the present embodiment, each inclined groove 544 and each linear groove 543 are formed so as to penetrate the side wall 541 in the present embodiment. However, the present invention is not limited thereto and they may not penetrate the side wall 541. Note that the inclined grooves 544 are the same as each other and the linear grooves 543 are the same as each other. Therefore, one inclined groove 544 and one linear groove 543 will be representatively described below.

The linear groove 543 is formed in a linear shape in the axial direction of the outer cylinder 54. In addition, the inclined groove 544 is formed so as to be inclined at a predetermined angle with respect to the axis of the outer cylinder 54. In addition, the inclined groove 544 is formed to be shorter than one turn. The proximal portion of the linear groove 543 and the distal portion (left end portion in FIG. 1) of the inclined groove 544 communicate with each other.

When the outer cylinder 54 moves in the axial direction, the inner plunger 51 is rotated to the right side in FIG. 1 with respect to the outer cylinder 54 at a predetermined angle due to the inclined groove 544 and the spur 513 of the inner plunger 51. More specifically, the inner plunger 51 rotates with respect to the outer cylinder 54, the inner cylinder 53, and the outer plunger 52. Note that a rotary mechanism (rotary portion), in which an engagement state or a released state can be selected by relatively rotating the spurs 32 of the administration restricting member 3 and the concave portion 517 of the inner plunger 51 around the central axis of the structure 1, is constituted by the inclined groove 544 of the outer cylinder 54 and the spur 513 of the inner plunger 51.

Here, in an unused state (initial state) shown in FIGS. 1 to 3, the spur 513 is positioned in the distal portion of the inclined groove 544. In this state, the rib row 515 of the inner plunger 51 is positioned at a position of the elongated hole 526 of the outer plunger 52 and the spur 32 of the administration restricting member 3 is engaged with the concave portion 517 between two adjacent ribs 516. Accordingly, the movement of the operation member 5 to the cylindrical body 2 in the distal direction is inhibited.

As shown in FIGS. 9 to 11, when the outer cylinder 54 moves to the inner cylinder 53 in the distal direction, the inner plunger 51 rotates to the right side in FIG. 9 with respect to the outer cylinder 54, the inner cylinder 53, and the outer plunger 52 and the spur 513 moves to the proximal portion of the inclined groove 544, due to the inclined groove 544 and the spur 513. In this state, the rib row 515 of the inner plunger 51 is positioned at a position (deviated position) that is retreated from the position of the elongated hole 526 of the outer plunger 52 in the circumferential direction, and the engagement between the spur 32 of the administration restricting member 3 and the concave portion 517 is released. Accordingly, the operation member 5 can move to the cylindrical body 2 in the distal direction.

In addition, eight elastic arm portions 545 are protrusively formed in the inner peripheral portion of the distal portion of the side wall 541 in the distal direction. The arm portions 545 are disposed along the circumferential direction of the side wall 541. Each claw 546 that inwardly protrude is formed in the distal portion of each arm portion 545. Each arm portion 545 and each claw 546 are disposed between the adjacent protruding piece 534 and protruding piece 535 of the inner cylinder 53, and the separation of the inner cylinder 53 from the outer cylinder 54 is inhibited by each claw 546 being engaged with the distal portion of the inner cylinder 53.

The pressing mechanism 40 has a function of generating pressing force for pressing the gasket 8, that is, a function of generating pressing force for pressing the gasket 8 through the inner plunger 51 and the outer plunger 52 of the operation member 5. In the present embodiment, the pressing mechanism 40 is configured to have a pair of coil springs (extension coil springs: second biasing members) 401. The proximal portion of each coil spring 401 is supported by the hook 525 of the outer plunger 52 and the distal portion thereof is supported by the hook 33 of the administration restricting member 3, in an extended state. Accordingly, each coil spring 401 biases the structure 1 and the operation member 5 in a direction approaching each other. That is, each coil spring 401 generates pressing force for pressing the gasket 8 in the distal direction through the inner plunger 51 and the outer plunger 52 of the operation member 5. Accordingly, it is possible to easily move the operation member 5 in the distal direction.

Note that the constituent material of the coil spring 401 is not particularly limited, and for example, it is possible to use the same material as that of the constituent material of the coil spring 13.

The pressing force transmission inhibiting mechanism 50 has a function of inhibiting transmission of force of the coil spring 401 (pressing mechanism 40) to the gasket 8 in the middle of the pressing operation. In addition, the pressing force transmission inhibiting mechanism 50 has the aforementioned function of inhibiting the transmission of the pressing force of the pressing mechanism 40 to the gasket 8 even in the unused state (initial state). In addition, the pressing force transmission inhibiting mechanism 50 has a function of changing the state of the pressing mechanism 40 from a state in which the pressing force of the pressing mechanism 40 is inhibited from being transmitted to the gasket 8 to a state where the pressing force is transmitted to the gasket 8. In the present embodiment, the pressing force transmission inhibiting mechanism 50 is constituted by each spur 32 of the administration restricting member 3 and each rib row 515 of the inner plunger 51, and can take an engagement state in which transmission of pressing force of the pressing mechanism 40 to the gasket 8 is inhibited in the middle of the pressing operation due to the engagement between the spur 32 of the administration restricting member 3 and the concave portion 517 of the inner plunger 51, and a released state in which the pressing force of the pressing mechanism 40 is transmitted to the gasket 8 by release of the engagement state. Note that the action of the pressing force transmission inhibiting mechanism 50 will be described in the description of a method of using the liquid administration device 10 to be described later.

Next, the method of using the liquid administration device 10 and an operation state in use of the liquid administration device will be described with reference to FIGS. 1 to 3 and 9 to 20.

[1] As shown in FIGS. 1 to 3, the liquid administration device 10 in an unused state (initial state) is prepared. In the liquid administration device 10 in the unused state, the cover member 6 covers the distal side needle tip of the double ended needle 71 at a first position. Note that in the unused state, a state is maintained in which the distal side needle tip of the double ended needle 71 is covered by the cover member 6 due to the biasing force of the coil spring 13.

Accordingly, erroneous puncturing due to the distal side needle tip of the double ended needle 71 can be reliably prevented.

In addition, in the puncture needle 7, the proximal side needle tip of the double ended needle 71 is separated from the sealing member 11 of the cylindrical body 2, and does not pierce the sealing member 11 yet. Accordingly, it is possible to maintain the liquid in an aseptic state until administration of the drug solution starts.

In addition, the spur 513 of the inner plunger 51 is positioned in the distal portion of the inclined groove 544 of the outer cylinder 54.

In addition, the rib row 515 of the inner plunger 51 is positioned at a position of the elongated hole 526 of the outer plunger 52 and the spur 32 of the administration restricting member 3 is engaged with the concave portion 517 between the two adjacent ribs 516. Accordingly, the movement of the operation member 5 to the structure 1 (cylindrical body 2) in the distal direction is inhibited.

[2] Next, as shown in FIGS. 9 to 11, the operation member 5 of the liquid administration device 10 in the unused state is gripped, the distal end wall part 62 of the cover member 6 is attached to a living body, and the operation member 5 is pressed toward the distal direction.

Accordingly, the outer cylinder 54 moves to the inner cylinder 53 in the distal direction; the inner plunger 51 rotates to the right side in FIG. 9 with respect to the outer cylinder 54, the inner cylinder 53, and the outer plunger 52 due to the inclined groove 544 and the spur 513; and the spur 513 moves to the proximal portion of the inclined groove 544. In this state, the rib row 515 of the inner plunger 51 is positioned at a position (deviated position) that is retreated from the position of the elongated hole 526 of the outer plunger 52 in the circumferential direction, and the engagement between the spur 32 of the administration restricting member 3 and the concave portion 517 is released. Accordingly, the operation member 5 can move to the cylindrical body 2 in the distal direction.

[3] Next, as shown in FIGS. 12 to 14, when the operation member 5 is further continuously pressed toward the distal direction, the cover member 6 moves to the operation member 5 and the structure 1 in the proximal direction, that is, from the first position to the second position against the biasing force of the coil spring 13.

At this time, the distal side needle tip of the double ended needle 71 protrudes from the opening 621 of the distal end wall part 62 of the cover member 6 and puncturing of a living body with the distal side needle tip is performed. In addition, the distal end wall part 62 presses the support member 72 of the puncture needle 7 toward the proximal direction. Accordingly, it is possible to pierce the sealing member 11 of the cylindrical body 2 with the proximal side needle tip of the double ended needle 71, and thus, the double ended needle 71 puncturing the living body communicates with the cylindrical body 2.

The engagement between the spur 32 of the administration restricting member 3 and the concave portion 517 is released, and therefore, the operation member 5 moves in the distal direction due to the biasing force of the coil spring 401. Accordingly, the gasket 8 can move toward the distal direction. That is, the aforementioned pressing operation is performed, and therefore, it is possible to perform administration of a liquid. The gasket 8 is attached to the bottom part 22 of the cylindrical body 2, and the administration of a liquid is completed.

At this time, the spur 513 of the inner plunger 53 is positioned in the proximal portion of the inclined groove 544.

[4] Next, as shown in FIGS. 15 to 17, the pressing of the operation member 5 toward the distal direction is stopped; the distal end wall part 62 of the cover member 6 is separated from the living body; and the double ended needle 71 is removed from the living body.

Accordingly, the cover member 6 moves in the distal direction, that is, to the fifth position due to the biasing force of the coil spring 13, and the distal side needle tip of the double ended needle 71 is covered with the cover member. In this manner, the cover member 6 and the coil spring 13 function as a safety mechanism that prevents needle piercing accidents after use.

In addition, at this time, the outer cylinder 54 moves to the inner cylinder 53 in the proximal direction due to the biasing force of the protruding piece 534 of the inner cylinder 53; the inner plunger 51 rotates to the left side in FIG. 15 with respect to the outer cylinder 54, the inner cylinder 53, and the outer plunger 52 due to the inclined groove 544 and the spur 513; and the spur 513 moves to the distal portion of the inclined groove 544. In this state, the rib row 515 of the inner plunger 51 is positioned at a position of the elongated hole 526 of the outer plunger 52 and the spur 32 of the administration restricting member 3 is engaged with the concave portion 517.

[5] Here, during the administration of a liquid, in some cases, it is necessary to temporarily suspend the administration of the liquid when, for example, the pain due to the liquid is strong or the like. In this case, as shown in FIGS. 18 to 20, the pressing of the operation member 5 toward the distal direction is stopped; the distal end wall part 62 of the cover member 6 is separated from the living body; and the double ended needle 71 is removed from the living body. Alternately, the operation member 5 is slightly moved in the proximal direction or the pressing force is weakened.

Accordingly, the outer cylinder 54 moves to the inner cylinder 53 in the proximal direction due to the biasing force of the protruding piece 534 of the inner cylinder 53; the inner plunger 51 rotates to the left side in FIG. 18 with respect to the outer cylinder 54, the inner cylinder 53, and the outer plunger 52 due to the inclined groove 544 and the spur 513; and the spur 513 moves to the distal portion of the inclined groove 544. In this state, the rib row 515 of the inner plunger 51 is positioned at a position of the elongated hole 526 of the outer plunger 52; the spur 32 of the administration restricting member 3 is engaged with the concave portion 517; and the transmission of the biasing force of the coil spring 401 to the gasket 8 is inhibited (engagement state). That is, the positional relationship between the structure 1 and the operation member 5 in the central axis direction of the structure 1 is fixed and the movement of the operation member 5 to the structure 1 (cylindrical body 2) in the distal direction is inhibited, and accordingly, it is possible to prevent a liquid from discharging from the distal end of the double ended needle 71.

Then, the operation of pressing the operation member 5 toward the distal direction is restarted after, for example, the pain disappears. Accordingly, the outer cylinder 54 moves to the inner cylinder 53 in the distal direction; the inner plunger 51 rotates to the right side in FIG. 18 with respect to the outer cylinder 54, the inner cylinder 53 and the outer plunger 52 and the spur 513 moves to the proximal portion of the inclined groove 544, due to the inclined groove 544 and the spur 513; the rib row 515 of the inner plunger 51 moves to a position that is retreated from the position of the elongated hole 526 of the outer plunger 52 in the circumferential direction; the engagement between the spur 32 of the administration restricting member 3 and the concave portion 517 is released; the biasing force of the coil spring 401 is transmitted to the gasket 8; and the administration of a liquid is restarted (released state).

Note that the rib row 515 has a plurality of ribs 516 that are provided in parallel in the axial direction of the inner plunger 51, and therefore, the spur 32 of the administration restricting member 3 can be engaged with the concave portion 517 at a plurality of places in the axial direction of the inner plunger 51. For this reason, it is possible to engage the spur 32 of the administration restricting member 3 with any concave portion 517 of the inner plunger 51 even at any position of the inner plunger 51 positioned in the axial direction.

As described above, according to the liquid administration device 10 that has the pressing mechanism 40, it is possible to support the movement of the operation member 5 in the distal direction or to move the operation member 5 in the distal direction, using the biasing force of the coil spring 401. Accordingly, it is possible to easily and reliably administer a liquid even for users who have difficulty in performing the pressing operation of the operation member 5, for example, a person with a weak amount of force, a patient with rheumatism who has a pain or deformation in the finger, and the like.

For example, in a case where the pain due to a liquid is strong, when temporarily suspending the administration of a liquid, the movement of the operation member 5 to the cylindrical body 2 in the distal direction is inhibited by the engagement of the spur 32 of the administration restricting member 3 and the concave portion 517 of the inner plunger 51. Accordingly, the transmission of the biasing force of the coil spring 401 to the gasket 8 is inhibited, and therefore, it is possible to prevent the liquid from discharging from the distal end of the double ended needle 71. Furthermore, it is possible to restart the administration of a liquid by performing the pressing operation of the operation member 5 in the distal direction.

In addition, in the liquid administration device 10, a state where the spur 32 of the administration restricting member 3 and the concave portion 517 of the inner plunger 51 are engaged with each other and a state where the engagement between the spur 32 and the concave portion 517 is released are taken through due to rotation of the inner plunger 51 by performing the pressing operation of the operation member 5 and stopping the pressing operation. When rotating the inner plunger 51, there is no obstacle that inhibits the rotation of the inner plunger 51, and therefore, resistance force during the pressing operation of the operation member 5 is relatively small. That is, in the liquid administration device 10, the resistance force during the pressing operation of the operation member 5 is smaller than that in a case where a liquid administration device is configured such that a state where a spur and a concave portion is engaged and a state where the engagement is released are taken by a linear motion of a predetermined member. Accordingly, it is possible to easily perform the pressing operation and to easily administer a liquid.

Note that the pressing operation is set to be any operation of discharging a liquid from a needle tube using tensile force of coil spring or the like, or a sum of pressing force of a user, and tensile force of a coil spring or the like.

Second Embodiment

Figure 21:
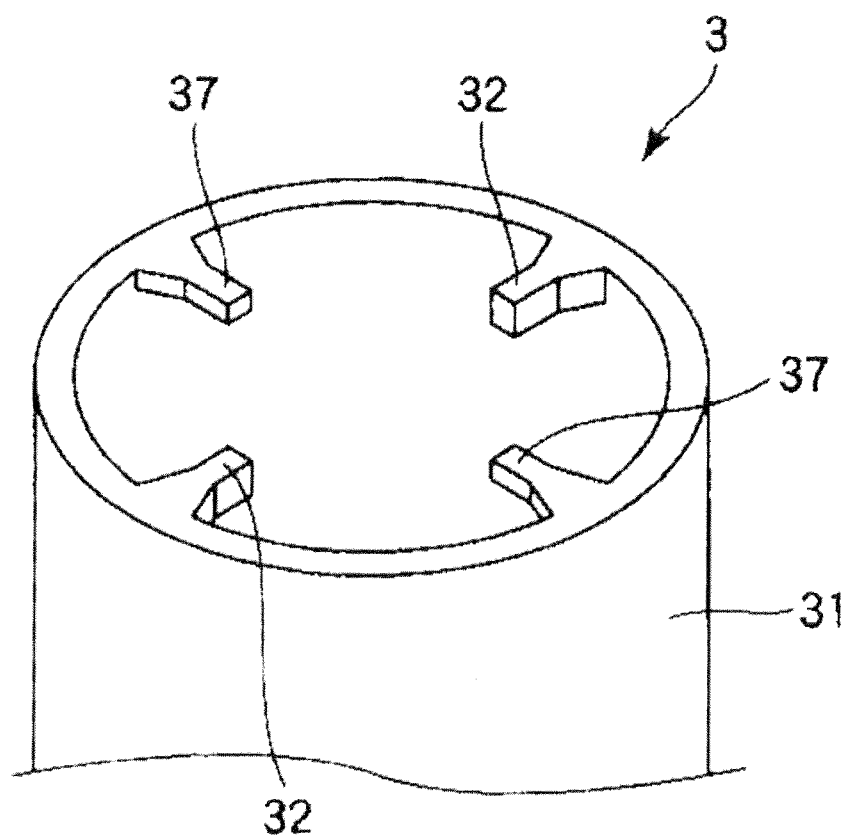
FIG. 21 is a perspective view of an administration restricting member of a structure of a liquid administration device of the present invention in a second embodiment.

FIG. 21 is a perspective view of an administration restricting member of a structure of a liquid administration device of the present invention in a second embodiment. Note that, hereinafter, the upper side is described as "proximal end (rear end)" or "upper (upward)", the lower side is described as "distal end" or "lower (downward)", and the vertical direction is described as "axial direction" or "longitudinal direction" in FIG. 21.

Hereinafter, in regard to the second embodiment, the difference between the second embodiment and the aforementioned first embodiment will be mainly described, and the description of the same matter will not be repeated.

A liquid administration device 10 of the second embodiment has a notification mechanism that notifies a user of information that discharging (administering) of a liquid is being performed. The notification mechanism has a vibration generating portion that notifies a user of a state of the discharging of a liquid through a pressing operation of an operation member 5, by generating a sound (audible sound) and a vibration and the vibration generating portion will be described below.

As shown in FIG. 21, a pair of elastic spurs 37 that are disposed so as to face each other is protrusively formed in an inner peripheral portion of a proximal portion of a main body portion 31 of an administration restricting member 3 at a central axis (inside) of the main body portion 31. The spurs 37 are respectively positioned between two spurs 37, and in the configuration shown in the drawing, at an intermediate position between the two spurs 37. Note that in the configuration shown in the drawing, the spur 37 has elasticity by making the thickness of the spur 37 thinner than that of the spur 32. The vibration generating portion is configured to have each spur 37 and each rib row 515 of an inner plunger 51.

Here, as described in the first embodiment, when the operation member 5 is pressed toward the distal direction by attaching a distal end wall part 62 of a cover member 6 to a living body, an outer cylinder 54 moves to an inner cylinder 53 in the distal direction. Moreover, the inner plunger 51 rotates to the right side in FIG. 9 with respect to the outer cylinder 54, the inner cylinder 53, and an outer plunger 52 and a spur 513 moves to the proximal portion of an inclined groove 544, due to the inclined groove 544 and the spur 513 (refer to FIGS. 9 to 11). In this state, the rib row 515 of the inner plunger 51 is positioned at a position (deviated position) that is retreated from the position of a elongated hole 526 of the outer plunger 52 in the circumferential direction, and the engagement between the spur 32 of the administration restricting member 3 and the concave portion 517 is released. Accordingly, the operation member 5 can move to the cylindrical body 2 in the distal direction.

In contrast, the rib row 515 of the inner plunger 51 and the spur 37 overlap each other when seen in a plan view. Accordingly, when the pressing operation is performed and the operation member 5 moves in the distal direction, the rib 516 of the rib row 515 climbs over the spur 37 through elastic deformation of the spur 37. At that moment, a sound (audible sound) and a vibration (click feeling) are generated from the spur 37.

A user feels the generated sound, and thus, it is possible to recognize that a liquid is being discharged. It is possible to recognize that the discharge of a liquid is completed when the sound is not generated. In addition, the generated vibration is transmitted to the outer cylinder 54, and the user feels the vibration and the sound. Accordingly, the user can more reliably recognize a state of a liquid being discharged and a state of a liquid that has completely discharged. According to the liquid administration device 10, the same effect as that in the aforementioned first embodiment can be obtained.

Hereinabove, the liquid administration device of the present invention has been described based on the embodiments shown in the drawings. However, the present invention is not limited thereto, and the configuration of each portion can be replaced with an arbitrary configuration that has an identical function. In addition, other arbitrary components may be added to the present invention.

In addition, the present invention may be obtained by combining two or more arbitrary configurations (characteristics) of each of the embodiments.

In addition, in the embodiments, the cylindrical body is filled with a liquid in advance. However, the present invention is not limited thereto, and for example, the cylindrical body may not be initially filled with a liquid and used by being filled with a liquid later.

In addition, in the embodiments, the first biasing member is a compression spring. However, the present invention is not limited thereto, and for example, the first biasing member may be a tensile spring or anything other than the spring.

In addition, in the embodiments, the second biasing member is a tensile spring. However, the present invention is not limited thereto, and for example, the second biasing member may be a compression spring or anything other than the spring.

In addition, in the present invention, the biasing mechanism (biasing portion) is not limited to the embodiments, and for example, may be a coil spring or the like.

In addition, in the present embodiment, the first engagement portion of the pressing force transmission inhibiting mechanism (pressing force transmission inhibiting portion) is provided in the structure and the second engagement portion is provided in the operation member. However, the present invention is not limited thereto, and for example, the first engagement portion of the pressing force transmission inhibiting mechanism may be provided in the operation member and the second engagement portion may be provided in the structure.

In addition, in the present embodiment, the puncture needle has a needle tube that is a double ended needle. However, the present invention is not limited thereto, and the puncture needle may have a needle tube without a needle tip on the proximal side. In this case, the needle tube communicates with the inner cylinder in advance (already in an unused state).

In addition, in the present embodiment, the inner cylinder 53 and the administration restricting member 3 are formed of different members from each other. However, the present invention is not limited thereto, and the inner cylinder and the administration restricting member may be integrally formed.

In addition, in the present embodiment, the inner plunger 51 and a plurality of ribs 516 (concave portions 517) are integrally formed. However, the present invention is not limited thereto, and the inner plunger and a member having the plurality of ribs may be formed of different members to each other.

In addition, in the present invention, when the administration of a liquid is completed and the distal side needle tip of the double ended needle 71 is covered by the cover member 6, a safety mechanism may be provided that maintains a state where the distal side needle tip of the double ended needle 71 is covered by the cover member 6. The safety mechanism can be configured as, for example, a mechanism that inhibits a movement of the cover member 6 to the cylindrical body 2 in the proximal direction. The cover member 6 cannot move in the proximal direction due to the safety mechanism, and therefore, it is possible to prevent needle piercing after use.

The liquid administration device of certain embodiments of the present invention includes: a structure that includes a cylindrical body that has a bottom part in a distal portion and an opening in a proximal portion and can be filled with a liquid therein, a needle tube that is positioned in the distal portion of the cylindrical body and has a sharp needle tip at a distal end, and a proximal end of which is communicable with the inside of the cylindrical body, and a gasket that is installed in the cylindrical body and is slidable along an axial direction of the cylindrical body; an operation member that performs a pressing operation in which the liquid is discharged from the needle tube through the gasket; a pressing portion that generates a pressing force for pressing the gasket; and a pressing force transmission inhibiting portion that inhibits transmission of the pressing force to the gasket in the middle of the pressing operation.

According to embodiments of the present invention, it is possible to prevent a liquid from being discharged from a distal end of a needle tube when temporarily suspending administration of the liquid since the present invention has a pressing force transmission inhibiting portion. In addition, it is possible to restart the administration of the liquid that is once suspended. Accordingly, it is preferable to prevent the liquid from being wasteful or insufficient, and to administer a sufficient amount of the liquid to a living body. Therefore, the present invention has industrial applicability.

What is claimed is:

1. A liquid administration device comprising:
   a structure that comprises:
      an administration restricting member comprising:
         a cylindrical main body portion, and
         a convex portion protruding inwardly from an inner surface of the cylindrical main body portion at a proximal end of the cylindrical main body portion,
      a cylindrical body disposed in the administration restricting member and comprising a bottom part in a distal portion and an opening in a proximal portion, the cylindrical body being fillable with a liquid, and
      a needle tube configured to be positioned in the distal portion of the cylindrical body, the needle tube having a sharp needle tip at a distal end, wherein a proximal end of the needle tube is communicable with an inside of the cylindrical body;
   a gasket installed in the cylindrical body, the gasket being slidable in an axial direction of the cylindrical body;
   an operation member configured to perform a pressing operation by pressing the gasket such that the liquid is discharged from the needle tube;
   a pressing mechanism configured to generate a pressing force for pressing the gasket; and
   a pressing force transmission inhibiting mechanism configured to inhibit transmission of the pressing force to the gasket during the pressing operation,
   wherein the pressing force transmission inhibiting mechanism comprises:
      a first engagement portion comprising the convex portion of the structure, and
      a second engagement portion provided in the operation member,
   wherein the pressing force transmission inhibiting mechanism is placeable in an engagement state in which the transmission of the pressing force to the gasket is inhibited due to engagement between the first engagement portion and the second engagement portion, and a released state in which the pressing force is transmitted to the gasket by release of the engagement state, during the pressing operation, wherein the liquid administration device further comprises a rotary mechanism configured to allow for selection between the engagement state and the released state, by relative rotation of the first engagement portion and the second engagement portion around a central axis of the structure, wherein the operation member is moveable with respect to the structure to a plurality of locations in an axial direction of the operation member, and wherein the second engagement portion is engageable with the first engagement portion after movement of the operation member with respect to the structure to each of the plurality of locations in the axial direction of the operation member.

2. The liquid administration device according to claim 1, wherein the pressing force transmission inhibiting mechanism is configured to inhibit the transmission of the pressing force by rotation of at least one of the operation member and the structure around the central axis.

3. The liquid administration device according to claim 1, wherein, in the engagement state, a positional relationship between the structure and the operation member in a central axis direction of the structure is fixed, and accordingly, the transmission of the pressing force to the gasket is inhibited.

4. The liquid administration device according to claim 3, wherein the operation member comprises a plunger, wherein the second engagement portion is provided in the plunger of the operation member, wherein the operation member comprises an outer cylinder that is disposed outside the structure, wherein the rotary mechanism comprises:
  an inclined rail portion provided in the outer cylinder, and
  a slider portion provided in the plunger, the slider portion being movable along the inclined rail portion, and wherein the plunger is configured so as to relatively rotate around the central axis with respect to the outer cylinder by the slider portion moving relative to the outer cylinder along the rail portion.

5. The liquid administration device according to claim 1, wherein the second engagement portion comprises a plurality of concave portions which are provided in parallel along the axial direction of the operation member and are engageable with the convex portion, and wherein in the engagement state, the convex portion and at least one of the plurality of concave portions are engaged with each other, a positional relationship between the structure and the operation member in a central axis direction of the structure is fixed, and accordingly, the transmission of the pressing force to the gasket is inhibited.

6. The liquid administration device according to claim 5, wherein the operation member comprises a plunger, wherein the second engagement portion is provided in the plunger of the operation member, wherein the operation member comprises an outer cylinder that is disposed outside the structure, wherein the rotary mechanism comprises:
  an inclined rail portion provided in the outer cylinder, and
  a slider portion provided in the plunger, the slider portion being movable along the inclined rail portion, and wherein the plunger is configured so as to relatively rotate around the central axis with respect to the outer cylinder by the slider portion moving relative to the outer cylinder along the rail portion.

7. The liquid administration device according to claim 1, wherein the operation member comprises a plunger, wherein the second engagement portion is provided in the plunger of the operation member, wherein the operation member comprises an outer cylinder that is disposed outside the structure, wherein the rotary mechanism comprises:
  an inclined rail portion provided in the outer cylinder, and
  a slider portion provided in the plunger, the slider portion being movable along the inclined rail portion, and wherein the plunger is configured so as to relatively rotate around the central axis with respect to the outer cylinder by the slider portion moving relative to the outer cylinder along the rail portion.

8. The liquid administration device according to claim 1, wherein the liquid is a drug solution.

9. The liquid administration device according to claim 1, wherein the pressing mechanism comprises at least one coil spring.

10. The liquid administration device according to claim 1, wherein the operation member comprises an inner plunger that is interlocked with the gasket, wherein the inner plunger comprises:
  a rod-shaped main body portion, and
  first and second rib rows that extend in an axial direction of the plunger, each of the first and second rib rows comprising a plurality of ribs, each rib of the plurality of ribs extending partially circumferentially around the main body portion of the inner plunger, and wherein the second engagement portion comprises the plurality of first and second rib rows.

11. A liquid administration device comprising:
a structure that comprises:
  a cylindrical body comprising a bottom part in a distal portion and an opening in a proximal portion, the cylindrical body being fillable with a liquid, and
  a needle tube configured to be positioned in the distal portion of the cylindrical body, the needle tube having a sharp needle tip at a distal end, wherein a proximal end of the needle tube is communicable with an inside of the cylindrical body;
a gasket installed in the cylindrical body, the gasket being slidable in an axial direction of the cylindrical body;
an operation member configured to perform a pressing operation by pressing the gasket such that the liquid is discharged from the needle tube, the operation member comprising:
  an outer cylinder that is disposed outside the structure and that comprises a plurality of inclined grooves that are inclined with respect to an axis of the outer cylinder,
  an inner plunger comprising a plurality of spurs, each of which is engaged with a corresponding one of the plurality of inclined grooves, and an inner cylinder that is disposed inside the outer cylinder and comprises:
  a cylindrical main body, and
  a plurality of elastic protruding pieces that protrude distally and radially outward from a distal end of the cylindrical main body;
a pressing mechanism configured to generate a pressing force for pressing the gasket; and
a pressing force transmission inhibiting mechanism configured to inhibit transmission of the pressing force to the gasket during the pressing operation,
wherein the pressing force transmission inhibiting mechanism comprises:
  a first engagement portion provided in one of the structure and the operation member, and
  a second engagement portion provided in the other one of the structure and the operation member,
wherein the pressing force transmission inhibiting mechanism is placeable in an engagement state in which the transmission of the pressing force to the gasket is inhibited due to engagement between the first engagement portion and the second engagement portion, and a released state in which the pressing force is transmitted to the gasket by release of the engagement state, during the pressing operation,
wherein the liquid administration device further comprises a rotary mechanism configured to allow for selection between the engagement state and the released state, by relative rotation of the first engagement portion and the second engagement portion around a central axis of the structure,
wherein the operation member is moveable with respect to the structure to a plurality of locations in an axial direction of the operation member, and
wherein the second engagement portion is engageable with the first engagement portion after movement of the operation member with respect to the structure to each of the plurality of locations in the axial direction of the operation member, and
wherein the plurality of elastic protruding pieces are configured to bias the outer cylinder in a proximal direction, and thereby cause the inner plunger to rotate until the pressing force transmission inhibiting mechanism is in the engagement state.

* * * * *